(12) United States Patent
Lai et al.

(10) Patent No.: US 6,791,688 B2
(45) Date of Patent: Sep. 14, 2004

(54) SYSTEMS AND METHODS FOR ANALYZING MIXTURES USING FLUORESCENSE

(75) Inventors: Chee Kong Lai, Littleton, MA (US); Charles Cooney, Brookline, MA (US); James C. Leung, Weston, MA (US); David P. Hoult, Saint Petersburg, FL (US); Peter Hanson, Canaan, NY (US); G. K. Raju, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/126,916

(22) Filed: Apr. 19, 2002

(65) Prior Publication Data

US 2003/0063279 A1 Apr. 3, 2003

Related U.S. Application Data

(63) Continuation of application No. PCT/US00/29129, filed on Oct. 20, 2000.
(60) Provisional application No. 60/160,537, filed on Oct. 20, 1999.

(51) Int. Cl.⁷ .............................................. G01N 21/64
(52) U.S. Cl. .................................... 356/417; 250/458.1
(58) Field of Search ............................... 356/317, 318, 356/417; 250/458.1, 459.1, 461.1, 461.2

(56) References Cited

U.S. PATENT DOCUMENTS

| | | | |
|---|---|---|---|
| 4,421,772 A | | 12/1983 | Munck et al. |
| 5,504,332 A | * | 4/1996 | Richmond et al. ...... 250/339.12 |
| 5,700,370 A | | 12/1997 | Helmo |
| 5,719,216 A | * | 2/1998 | Schermer et al. ............. 524/68 |
| 5,854,216 A | * | 12/1998 | Gaudreau ..................... 514/12 |
| 5,859,708 A | * | 1/1999 | Feldman ..................... 356/406 |
| 5,946,083 A | * | 8/1999 | Melendez et al. .......... 356/317 |
| 5,946,088 A | * | 8/1999 | Aldridge ...................... 356/300 |
| 6,060,318 A | * | 5/2000 | Moeggenborg et al. ........ 436/3 |
| 6,089,458 A | * | 7/2000 | Lake ........................... 235/488 |
| 6,122,042 A | | 9/2000 | Wunderman et al. |
| 6,274,110 B1 | * | 8/2001 | Kim et al. ................... 423/263 |

FOREIGN PATENT DOCUMENTS

| | | |
|---|---|---|
| EP | 0 122 741 | 10/1984 |
| EP | 0 877 079 A1 | 11/1998 |
| JP | 06 088788 A | 3/1994 |
| WO | WO 98/57153 A1 | 12/1998 |

OTHER PUBLICATIONS

Randall, Tina S., "Analysis of the Introduction of New Technologies to Evaluate the Performance of Pharmaceutical Unit Operations," B.S. in Industrial Biochemical Engineering, Autonomous Metropolitan University (1994), Submitted to the Technology and Policy program in partial fulfillment of the requirements for the degree of Master of Science in Technology and Policy at the Massachusetts Institute of Technology, Jun. 1998, pp. 1–112. Thesis Supervisor: Professor Charles L. Cooney (Professor of Chemical Engineering).

Oh, S–T., et al., "Effect of particle size distribution and mixing homogeneity on microstructure and strength of alumina/copper composites," Nanostructured Materials, pp. 327–332, vol. 10, No. 2, 1998, pp. 327–332, XP004140580. Elsevier, New York, NY, US., ISSN: 0965–9773.

* cited by examiner

Primary Examiner—F. L. Evans

(57) ABSTRACT

The invention provides systems and methods for analyzing mixtures and, particularly during processing of the mixtures. The invention provides systems and methods for analyzing mixtures and, particularly, for analyzing mixtures during processing. The methods and systems utilize fluorescence to non-invasively analyze one or more components of the mixture. The analysis may provide a variety of compositional information such as the chemical identity of components, the concentration of components, the uniformity of the mixture and other information. A number of different types of processing equipment can be configured to provide the analysis and, accordingly, the analysis may be performed during a number of processing operations. The system and methods are particularly useful in processing mixtures which are preferably homogeneous blends, such as pharmaceutical products.

95 Claims, 29 Drawing Sheets

SYSTEMS AND METHODS FOR ANALYZING MIXTURES USING FLUORESCENSE

RELATED APPLICATIONS

This application is a continuation of International Patent Application Serial No. PCT/US00/29129, filed Oct. 20, 2000, which is a PCT of U.S. Provisional Patent Application Ser. No. 60/160,537, filed Oct. 20, 1999.

FIELD OF INVENTION

The present invention relates generally to materials analysis and, more particularly, to systems and methods which use fluorescence to analyze mixtures.

BACKGROUND OF THE INVENTION

Many areas of materials processing involve mixing several components to form a final product. The uniformity of the mixture and concentration of particular components may both be critical to the quality of the final product, for example, in the preparation of pharmaceuticals. Many pharmaceutical processes, for example, employ analytical steps to assess the uniformity of the mixture and/or the concentration of a component, such as the active drug ingredient. Such steps may be used during process development efforts to optimize process variables or during commercial manufacturing processes, for example, as a quality control measure.

One conventional method for analyzing mixtures during processing involves physically removing a sample from the mixture and determining its composition by any number of analytical techniques known in the art. Generally, these methods may be susceptible to sampling and processing errors. For example, the composition of the sample may not be indicative of the actual mixture and it may be difficult to maintain consistent sampling procedures. The accuracy of the compositional measurements, therefore, may be compromised. In addition, the sampling procedure is invasive and, thus, disrupts the process. Furthermore, the methods can be time consuming and cumbersome to execute.

Another method for analyzing a mixture during processing involves using near infrared (NR) spectral analysis. Such a method has been disclosed, for example, in Aldridge, U.S. Pat. No. 5,946,088. This method generally is used to analyze the homogeneity and potency of a mixture on-line. However, because the method employs NIR spectral analysis, it may be limited in its sensitivity, specificity for the types of materials which can be analyzed, and its speed of analysis.

Accordingly, a need exists for an improved technique for analyzing mixtures during processing.

SUMMARY OF THE INVENTION

The invention provides systems and methods for analyzing mixtures and, particularly, for analyzing mixtures during processing. The methods and systems utilize fluorescence to non-invasively analyze one or more components of the mixture. The analysis may provide a variety of compositional information such as the chemical identity of components, the concentration of components, the uniformity of the mixture and other information. A number of different types of processing equipment can be configured to provide the analysis and, accordingly, the analysis may be performed during a number of processing operations. The system and methods are particularly useful in processing mixtures which are preferably homogeneous blends, such as pharmaceutical products.

In one aspect, the invention provides a method of processing materials. The method includes measuring the uniformity of a mixture of more than one component using fluorescence during processing of the mixture.

In another aspect, the invention provides a method of processing materials. The method includes non-invasively analyzing a mixture of more than one component using fluorescence during processing of the mixture.

In another aspect, the invention provides a method of processing materials. The method includes measuring the concentration of a component of a mixture using fluorescence during processing of the mixture.

In another aspect, the invention provides a method of materials analysis. The method includes measuring the concentration of at least one solid component of a mixture using fluorescence.

In another aspect, the invention provides a method of processing materials. The method includes measuring the stability of a mixture of more than one component of a mixture using fluorescence during processing of the mixture.

In another aspect, the invention provides a method of materials analysis. The method includes processing a mixture of more than one component in a processing apparatus, transferring the mixture from the processing apparatus, and measuring the concentration of a component of the mixture remaining in the processing apparatus, after transferring the mixture, using fluorescence.

In another aspect, the invention provides a system for processing materials. The system includes a processing apparatus configured to process a mixture of more than one component. The system further includes a fluorescence instrument operatively associated with the processing apparatus capable of measuring the uniformity of the mixture during processing of the mixture.

In another aspect, the invention provides a system for processing materials. The system includes a processing apparatus configured to process a mixture of more than one component. The system further includes a 1 fluorescence instrument operatively associated with the processing apparatus capable of non-invasively analyzing the mixture using fluorescence during processing of the mixture.

In another aspect, a system for processing materials is provided. The system includes a processing apparatus configured to process a mixture of more than one component. The system further includes a fluorescence instrument operatively associated with the processing apparatus capable of measuring the concentration of one component of the mixture during processing of the mixture.

Among other advantages, the invention provides systems and methods for non-invasively measuring the uniformity and/or the concentration of a component during processing. As a result, the process is not disturbed by the analysis and is, generally, not susceptible to the sampling and measurement errors associated with conventional invasive methods of analysis. Furthermore, the analysis may be conducted on-line and in real-time to provide compositional information during the process. This permits adjustment of processing variables to optimize the process.

LIF analysis also provides a strong signal which may result in a higher sensitivity and specificity than achievable in NIR analysis. In particular, this higher sensitivity enables the systems and methods of the invention to be used to detect species at low concentrations, for example, active ingredients in certain pharmaceutical products. The higher specificity permits highly accurate identification of compounds.

Furthermore, the LIF instrument used in the systems and methods of the invention may be readily used in conjunction with any number of types of processing equipment, especially equipment used in pharmaceutical processing. Generally, the LIF instrument is small, portable, and easily be mounted on a variety of different locations on processing equipment.

Various embodiments of the present invention provide certain advantages and overcome certain drawbacks of the conventional techniques. Not all embodiments of the invention share the same advantages and those that do may not share them under all circumstances. Other advantages, novel features, in aspects of the invention will become apparent from the following detailed description of the invention when considered in conjunction with the accompanying figures, and from the claims.

DETAILED DESCRIPTION OF THE INVENTION

The invention provides systems and methods for analyzing mixtures using fluorescence. The invention involves using fluorescence to obtain compositional information of the mixture, such as the identity of a component, the concentration of a component and the uniformity of the mixture. Various types of processing equipment, as described further below, can be configured to non-invasively analyze a mixture during processing using fluorescence. The systems and methods of the invention can be used to analyze any number of different types of mixtures and different components thereof including solids.

The term "during processing," as used herein, refers to any time during the production of a product from initial product component/ingredient formation to final product delivery. "During processing" encompasses the time during active processing steps, as defined below, as well as time between active processing steps, such as storage time. "During processing" can be used to describe process development efforts, as well as, commercial manufacturing processes.

The term "active processing steps," as used herein, refers to steps which involve actual processing of a mixture. In pharmaceutical processing, active processing steps may include bulk active production steps, bulk formulation steps (e.g., mixing, transportation, and the like), and fill and finishing steps (tablet and/or capsule formation).

The term "non-invasive," as used herein, describes a measurement technique that does not stop or slow an active processing step while taking the measurement.

Figure 3:
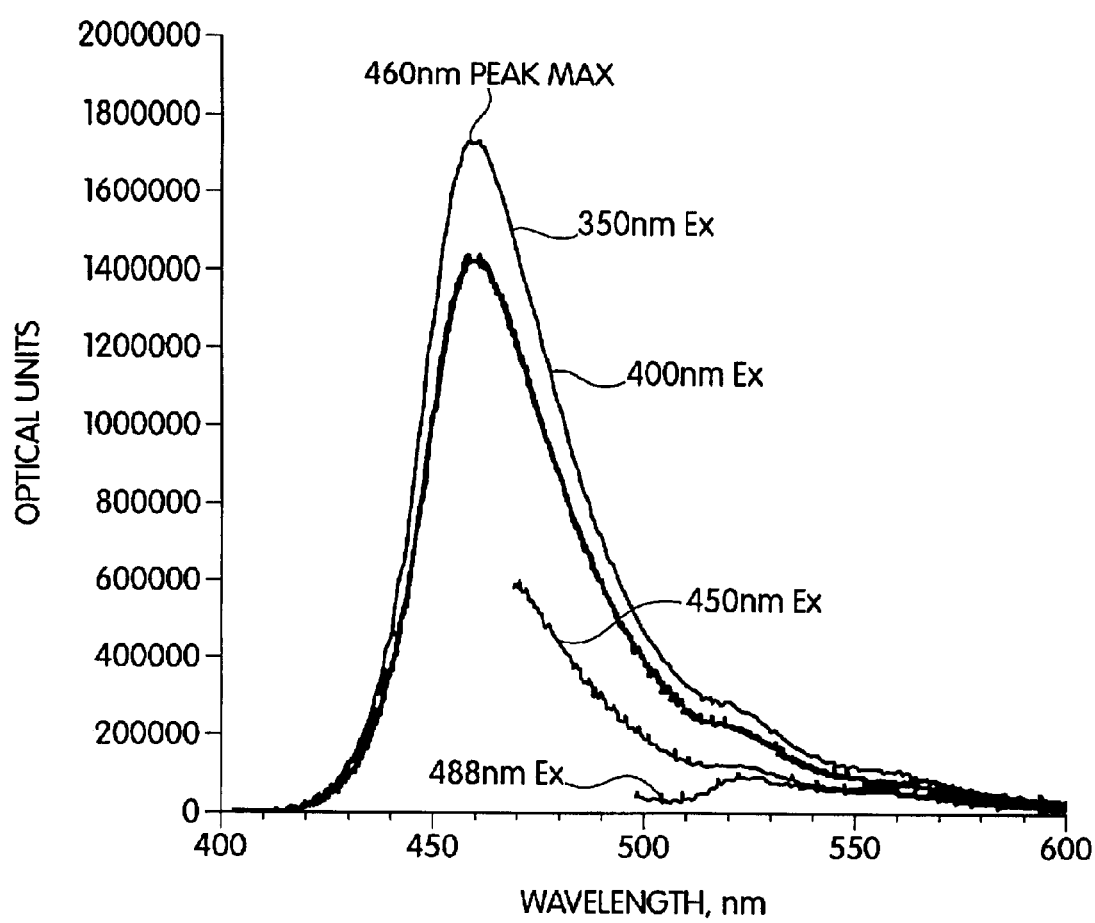
FIG. 3 shows the solid-phase fluorescence spectra of triamterene at different excitation wavelengths.

The invention measures the fluorescent properties of compounds. In most embodiments, fluorescence in at least one compound of a mixture is induced by exposing the mixture to light radiation in a technique known as light-induced fluorescence (LIF). However, in other embodiments the natural fluorescence of compounds may be measured. LIF, as used herein, may utilize any type of electro-magnetic radiation to induce fluorescence. In the LIF technique, the light radiation can cause electronic transitions within the molecules of the components of the mixture. These transitions, in many compounds, can result in the emission of radiation in a process known as fluorescence. The energy of the emitted radiation is detected to collect a fluorescence spectrum. Compounds have characteristic fluorescence spectra depending upon their electronic structure. (For example, a fluorescence spectra of triamterene is illustrated in FIG. 3.) The spectra, therefore, provides information regarding the composition of the material.

LIF analysis has several features which makes it particularly suitable for use in the methods and systems of the present invention. LIF can be conducted non-invasively and, thus, processes do not have to be stopped or slowed in any manner by the analysis. In addition, LIF is a non-destructive technique, that is, the technique does not consume any material. Therefore, the composition of the mixture is generally unaffected by the analysis.

LIF also provides a rapid sampling rate which permits obtaining compositional data on-line and in real time. As used herein, "on-line" refers to a system or method in which data is fed directly from the fluorescence detecting instrument to a data processing system and the results are obtained and can be analyzed during the processing of input data reception. As used herein, "real-time" refers to a system or method that processes data at the same speed as data is received from the fluorescence detecting instrument.

Furthermore, LIF may provide a strong fluorescent signal which can result in a high-detection sensitivity. Consequently, small concentrations of components, in some cases down to 0.1% or lower of the total mixture by weight, can readily be measured using LIF. Such small concentrations of active drug components, for example, are oftentimes used in pharmaceutical processes. In addition, because fluorescent spectra are characteristic of the specific chemical composition of compounds, LIF may be used to identify the composition of compounds within a mixture.

Figure 1:
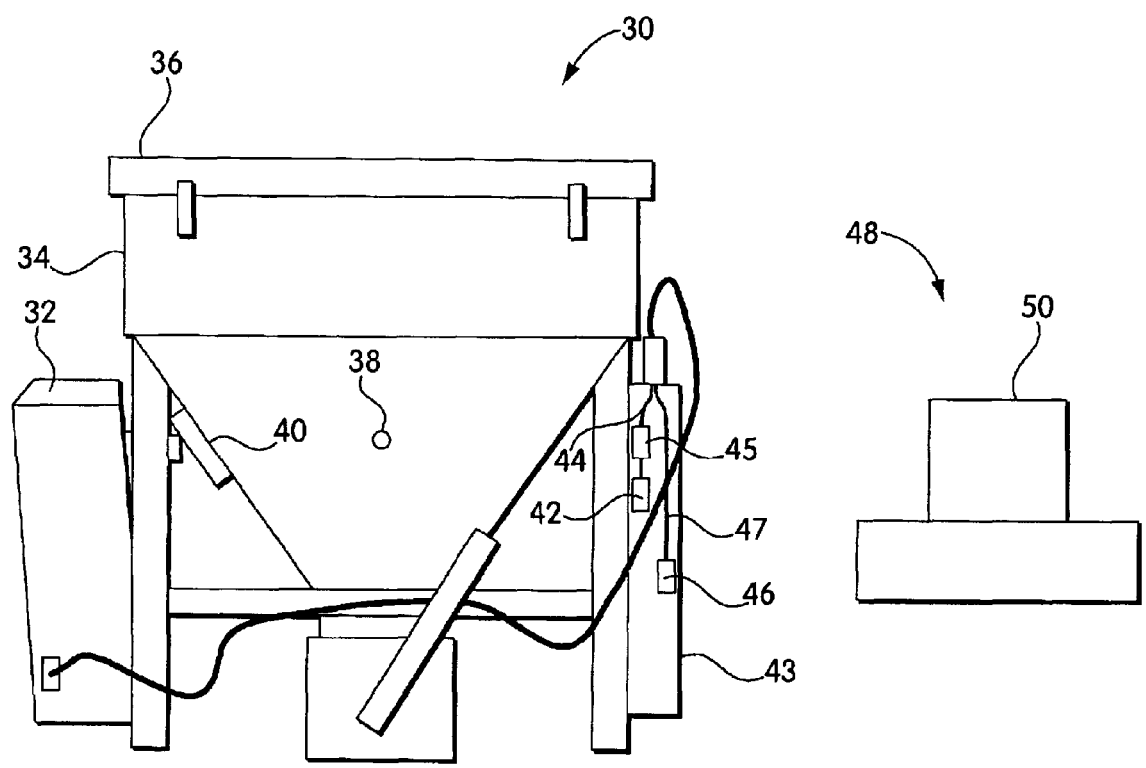
FIG. 1 schematically illustrates a blender for processing pharmaceutical material including an LIF instrument according to one embodiment of the invention.

One illustrative embodiment of a processing apparatus configured for LIF analysis according to the invention is shown schematically in FIG. 1. A mixing apparatus 30 for use in pharmaceutical processing includes an LIF instrument 32 mounted externally on a bin blender 34. In the illustrative embodiment, the bin blender has a capacity of 2.5 cubic feet, though other sizes may be used in other embodiments. The components which comprise the mixture may be added to the bin blender by removing a lid 36 which is otherwise secured to confine the mixture. The bin blender, including the mounted LIF instrument, is constructed to rotate in a clockwise direction about an axis 38 to mix the components until the mixture is uniform, as described further below.

A window 40 in the exterior of the bin blender 34 provides access to the mixture for the LIF instrument 32. The window can be made of any material suitable for transmitting light including a UV grade glass, quartz, sapphire, and the like.

The LIF instrument, in the illustrative embodiment, is powered by a power supply 42 housed in an external unit 43 mounted to the bin blender. Power may be provided via a cable 44 which connects the power source to the LIF instrument. An on/off switch 45 may be connected to the power supply and also housed within external unit 43 to control activation of the LIF instrument. The on/off switch in preferred embodiments is designed to activate the LIF instrument based upon the position of the blender during its rotation cycle. Such switches are known in the art and generally include a position-detection mechanism. In certain preferred embodiments, on/off switch 45 is a mercury switch.

LIF instrument 32, in the illustrative embodiment, is connected to an RF converter 46 housed within external unit 43 via a cable 47. RF converter 46 receives voltages from the LIF instrument 32 proportional to the detected fluorescent signals, as described further below, and converts the voltages into radio frequencies. The radio frequencies are transmitted to a remote data acquisition system 48. The data acquisition system can be used to process and/or display the LIF data in real time, for example, on a display monitor 50. The data acquisition system may also store the LIF data for processing and analysis at a later time.

Figure 1A:
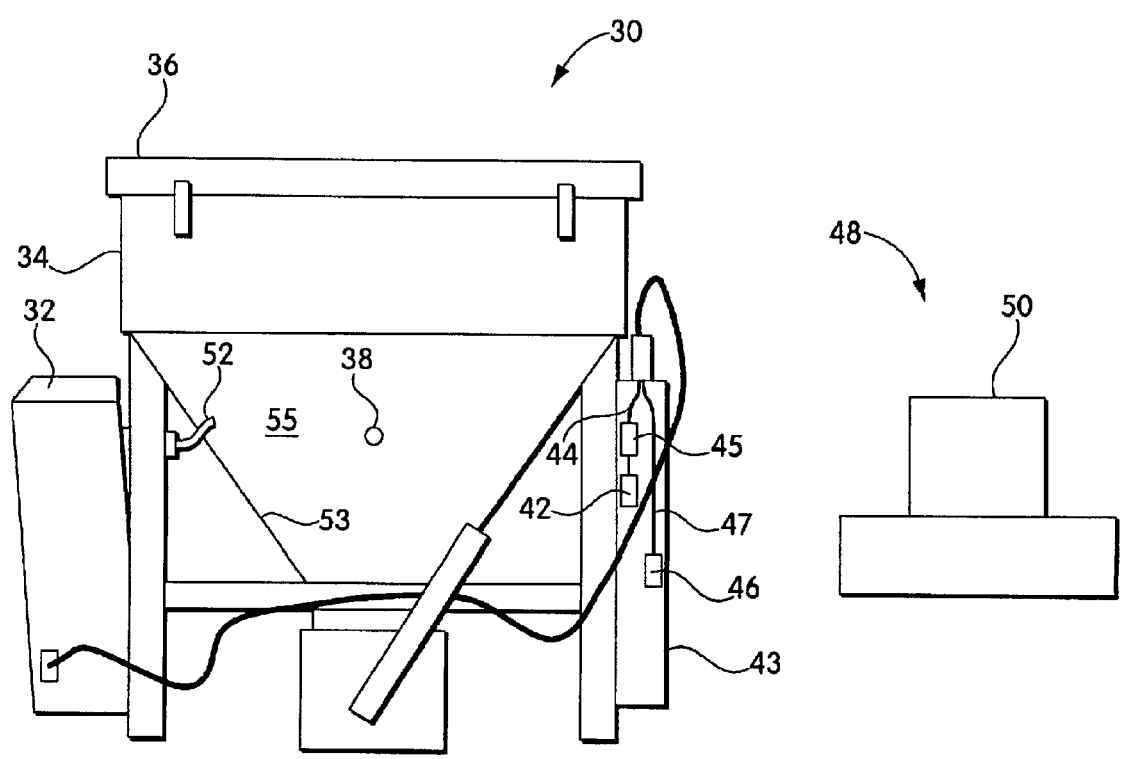
FIG. 1A schematically illustrates a blender for processing pharmaceutical material including an LIF instrument having a fiber-optic probe inserted into a wall of the blender according to one embodiment of the invention.

In another illustrative embodiment of the invention shown in FIG. 1A, LIF instrument 32 includes a fiber-optic probe 52 which is inserted through a wall 53 of bin blender 34 into a processing space 55. The fiber-optic probe is constructed to carry light radiation provided by the LIF instrument and fluorescent signals emitted from the mixture, as described further below. The fiber-optic probe can be placed at any selected position in bin blender 34, thus permitting analysis at specific locations which may be advantageous in certain embodiments. In some embodiments, bin blender 34 may include than one fiber-optic probe which permits analysis at multiple positions simultaneously.

It is to be understood that the LIF instrument, though illustrated as a component of a mixing apparatus, could similarly be a component of any other type of processing equipment. Equipment used in pharmaceutical processing are particularly suitable to be configured for LIF analysis. Examples of such processing equipment include but are not limited to equipment for forming and handling pharmaceutical tablets, equipment for transporting mixtures (e.g. pipes, conduits, and the like) and equipment for storing mixtures during processing, such as storage bins.

Though the LIF instrument is attached directly to the blender in FIGS. 1 and 1A, other arrangements are also possible. The only requirement of the arrangement between the LIF instrument and the apparatus is that the LIF instrument has sufficient access to the material within the processing apparatus to perform the analysis. Oftentimes, the particular arrangement is dictated by the type of apparatus used. In certain embodiments, the LIF instrument may stand alone, that is, the instrument may not be physically attached to the processing apparatus. In certain embodiments, processing equipment may be equipped with more than one LIF instrument.

Any suitable type of data acquisition system may also be used in conjunction with the systems and methods of the invention. Though the illustrative embodiment includes a remote data acquisition system, in many cases, the data acquisition system may be connected directly to the LIF instrument. In these embodiments, for example, the LIF signal may be transmitted via a cable to the data acquisition system. In addition, the data acquisition system in certain embodiments, may simply serve to store the LIF data. In these cases, the data acquisition system may not include a display monitor. In other cases, the data acquisition system may store and manipulate the data, though without displaying the results.

Figure 2:
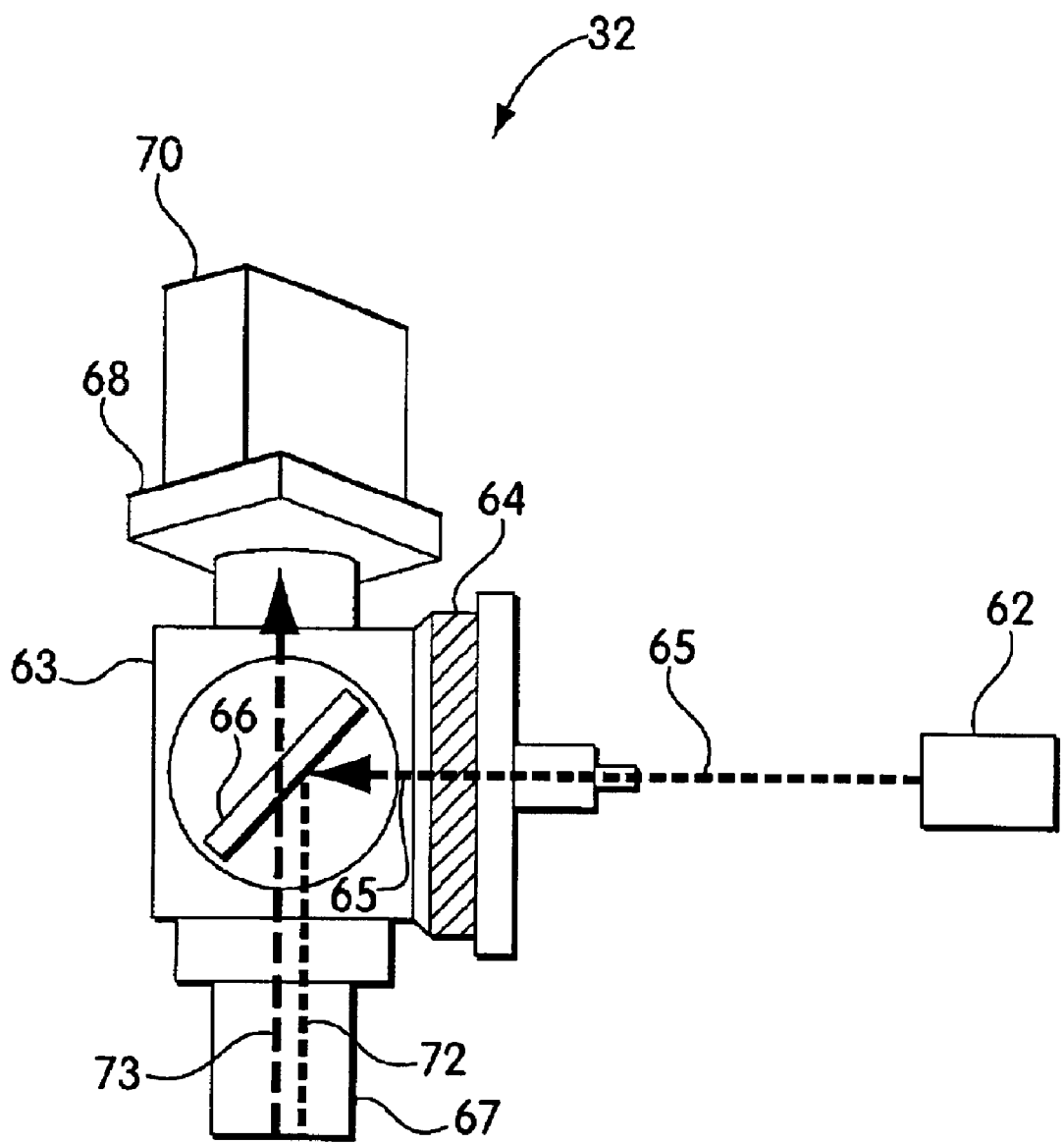
FIG. 2 schematically illustrates an LIF instrument according to one embodiment of the invention.

One illustrative embodiment of an LIF instrument is illustrated schematically in FIG. 2. LIF instrument 32 includes a light source 62 which is designed to emit light radiation, a portion of which follows path 65. The light source may be any of a number of suitable sources for stimulating fluorescence. In some embodiments, the light source is a laser, such as an argon laser. In other embodiments, the light source may emit radiation over a range of wavelengths, such as a flashlamp. These light sources have the advantage of providing a broad range of wavelengths from which specific excitation wavelengths can be chosen by the use of selected optical filters as described further below. In yet another embodiment, the light source may be a photolaser diode which is particularly suitable in embodiments that require miniaturization of the LIF instrument.

The LIF instrument further includes a lens unit 63 which houses several components that select and direct the excitation light and fluorescent light appropriately. A selection filter 64 of the lens unit is designed to permit light from the light source having a specific wavelength to pass therethrough continuing along path 65. The wavelength that passes therethrough, known as the excitation wavelength, is selected based upon the type of components being analyzed. Certain wavelengths may be more suitable for generating fluorescent signals from certain components. In some embodiments, the selection filter can be configured to permit multiple excitation wavelengths to pass therethrough. Multiple excitation wavelengths may be particularly useful for examining the fluorescence of more than one compound in a mixture. In some cases, using multiple excitation wavelengths can be used to reduce the signal/noise ratio by examining the fluorescent signal at different wavelengths.

A dichroic mirror 66 inside the lens unit 63 is designed and positioned to reflect a large portion, for example greater than about 80%, of the excitation light in the direction of the mixing chamber along path 72. An exit lens 67 focuses the excitation light reflected from the dichroic mirror into the mixing chamber. The fluorescent radiation from a sample enters the LIF instrument following path 73 and passes through the dichroic mirror. Typically, the fluorescent radiation is selected by a filter 68 positioned in front of a photomultiplier tube 70. The photomultiplier tube detects the fluorescent radiation and converts the signal to a voltage which may be further processed before being transmitted to the data acquisition system.

During operation of the illustrative embodiment, appropriate components are added to the bin blender through the opening at the top to form a mixture. Generally, in pharmaceutical processing, the components are powders and may be active ingredients (e.g. drugs) and excipients. The lid at the top of the blender is closed to confine the mixture and the blender is then rotated, typically, in a clockwise direction. The rotation speed is selected to appropriately mix the components and, generally, is between about 5 and about 50 rpm for most pharmaceutical processes. Typical mixing cycles in pharmaceutical processing are between about 5 and about 30 minutes, though the time will depend upon the individual process and materials used.

At any point or throughout the mixing cycle the LIF instrument may be activated and LIF measurements may be taken. When activated, the light source of the LIF instrument emits radiation. The radiation is filtered to the appropriate wavelength and reflected by the dichroic mirror into the mixing chamber. Components of the mixture absorb the radiation which stimulates at least one of the components to fluoresce. The fluorescent radiation is emitted in all directions and a portion passes through the window in the processing bin and, subsequently, through the dichroic mirror. After passing through the dichroic mirror, the fluorescent radiation is filtered and then detected by a photomultiplier tube receiver. The fluorescent signal may be converted to a voltage by the photomultiplier tube which may be further converted to an RF signal by the RF converter. The RF signal may be transmitted to the remote data acquisition system to provide on-line measurements which may be displayed on the monitor in real-time.

The systems and methods of the invention may be used to examine compositional information of a number of different components. Any component that emits fluorescent light, for example, may be analyzed. In some embodiments, the component analyzed is a solid. In some cases, the solid material is a powder. Such is the case as in many types of pharmaceutical processes. In other embodiments, the component analyzed may be a liquid.

The systems and methods of the invention may also be used to analyze a variety of different types of mixtures. In some embodiments, the mixture may consist essentially entirely of solid components. In other embodiments, the mixture may consist essentially of liquid components. In still other embodiments, the mixture may include solid and liquid components. In some cases, the mixture may be a semi-solid mixture. Such semi-solid mixtures are those of relatively high viscosity, between that of a liquid and a solid, that can be easily deformed and spread against skin using the hand, yet can be self-supporting (free rapid flow) at room temperature. Semi-solid mixtures may include creams which are semi-solid dosage forms containing one or more drug substances dissolved or dispersed in a suitable base. In other embodiments, the semi-solid mixture may be a gel consisting of either suspensions made up of small inorganic particles or large organic molecules and are penetrated by a liquid (also known as jellies). In other embodiments, the semi-solid mixtures are ointments which are preparations intended for external applications to the skin or mucous membranes. Other types of mixtures which may be analyzed include emulsions which are two-phase systems in which one liquid is dispersed throughout another liquid in the form of small droplets. In another set of embodiments, the mixture analyzed is a suspension which is a liquid preparation that includes solid particles dispersed throughout a liquid phase in which the particles are not soluble.

The systems and methods of the invention can be used to acquire any information which can be obtained using LIF analytical techniques. Such information generally relates to the composition of the mixture. LIF can be used, for example, to measure the concentration of components during processing. In pharmaceutical processing, the systems and methods can, thus, be used to measure concentration of the active drug ingredient which may be critical to its production. LIF analysis also may be used to obtaining information regarding the uniformity of mixtures. Typically, uniformity data is gathered by monitoring the concentration of a component over time. When the LIF signal of a component becomes constant over time, the mixture is uniform. As illustrated further in the examples below, mixing profiles may be generated which illustrate the concentration of a component as a function of the number of rotation cycles. LIF can also be used to identify chemical compounds in a mixture. Because compounds emit characteristic fluorescent spectra, LIF may be, thus, used to analyze the composition of components The compositional information can be used in process development, for example, to optimize and streamline processes. Furthermore, compositional information can be used as a quality control measure in the actual processing of final products. As discussed above, the systems and methods of the invention can be used with any type of materials in any industry, though pharmaceutical processing is a preferred application of the invention.

The function and advantage of these and other embodiments of the present invention will be more fully understood from the examples below. The following examples are intended to illustrate the benefits of the present invention, but do not exemplify the full scope of the invention.

EXAMPLE 1

Fluorescence Spectra of Pharmaceutical Compounds

Figure 4:
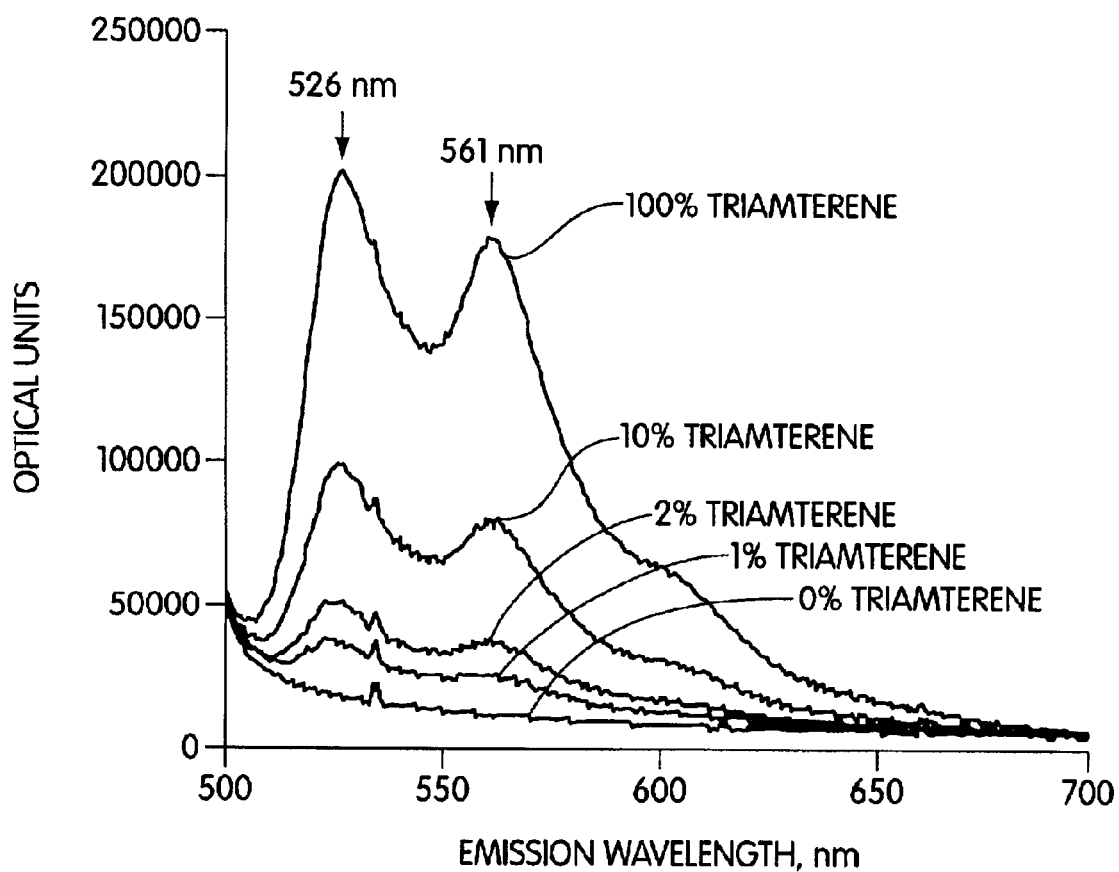
FIG. 4 shows a solid-phase fluorescence spectra of solid samples having a range of triamterene concentrations at an excitation energy of 488 nm.

LIF was used to generate a fluorescence spectra of solid-phase triamterene, a pharmaceutical compound, at a variety of excitation wavelengths as illustrated in FIG. 3. The results show that the amount of signal obtained from the induced fluorescence can be controlled by the excitation wavelength. An excitation wavelength of 488 nm (Argon laser) resulted in a lower induced fluorescence when compared to excitation at a wavelength of 350 nm. Depending on use, different excitation wavelengths may be preferred. In certain embodiments, to prevent saturation of the photomultiplier tube and to generate linear correlation between solid sample concentration and LIF signals, the reduced LIF signals stimulated by excitation at 488 nm may be advantageous. For example, as illustrated in FIG. 4, excitation wavelengths of 488 nm can still detect triamterene at 1% by total weight of mixture. In other embodiments requiring higher sensitivity, such as when measuring very low concentrations (0.1% and below) the excitation energy at lower wavelengths, for example 350 nm, may be required.

EXAMPLE 2

Usage of LIF to Non-Invasively Monitor Mixture Uniformity in Real-Time

Figure 5:
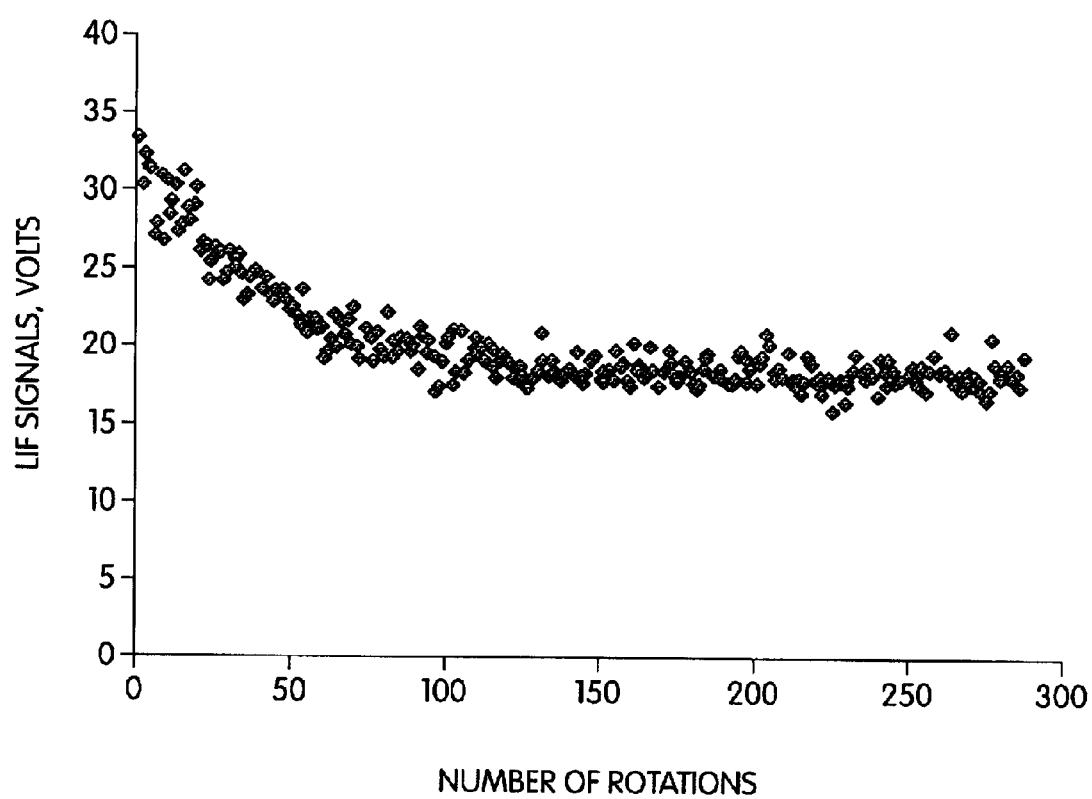
FIG. 5 shows a blending profile of the mixture described in Example 2.

A laboratory blending experiment was performed using a 20 mL tube tumbler to simulate a bin blender. The samples included a formulation of 10% triamterene-lactose by weight. The samples were tumbled for a total of 20 minutes at a blending speed of about 30 rpm. A laser beam (power= 0.04 mW) was positioned about ⅓ from the bottom of the powder level in the blender, where powder at relative constant bulk density was present most of the time. In addition, data acquisition was synchronized with the help of an infrared trigger and obtained in real-time. LIF signal characteristic of triamterene was measured as a function of the number of rotations to generate blending profiles. A typical blending profile is shown in FIG. 5 showing LIF signal versus the number of rotations.

The example illustrates the use of LIF to non-invasively monitor the uniformity of a mixture.

EXAMPLE 3

Usage of LIF to Examination of Powder Blending Kinetics

Figure 6:
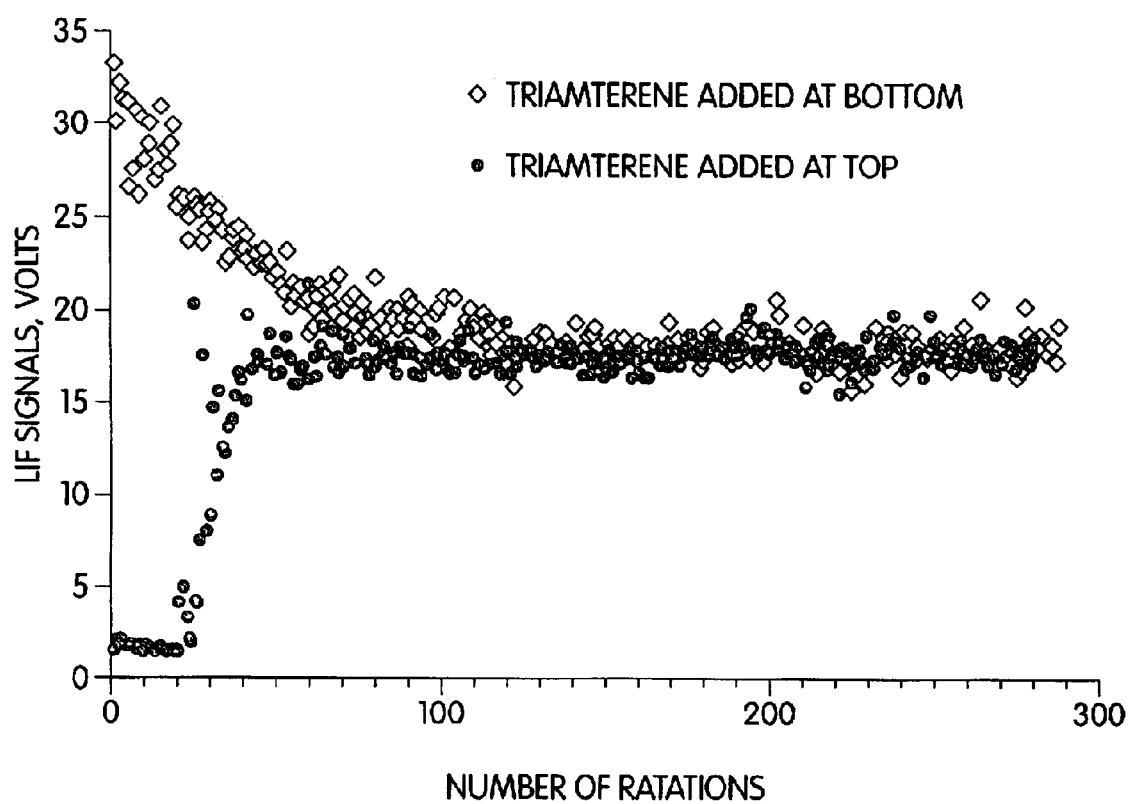
FIG. 6 shows blending profiles for mixtures loaded at the top and bottom of the blending vessel, respectively, as described in Example 3.

A 10% by weight triamterene-lactose formulation was used in two separate experiments. In the first experiment, triamterene was placed at the bottom of a mixing vessel and lactose was added on top of the triamterene. In the second experiment, lactose was placed at the bottom of the vessel and triamterene was added on top. The LIF instrument was positioned near the bottom of the vessel. In both cases, the blending process proceeded with synchronized data acquisition of the triamterene signal until blend homogeneity was obtained (~100 rotations). Mixing profiles were generated for both experiments and illustrated in FIG. 6.

Examination of the real time blending kinetics of the two separate experiments indicated distinct mixing differences in the early phases of the mixing process. In the first experiment, because of the proximity of the LIF instrument to the bottom of the vessel, the initial LIF signal was high followed by a slow decay over time as the powder mixed. The signal eventually stabilized to equilibrium when blend homogeneity was attained. In the second experiment, the initial LIF signal is low because lactose is preferentially located at the bottom of the vessel near the LIF instrument. As the mixing progressed, the triamterene signal increased until it equilibrated at blend homogeneity. When blend homogeneity was achieved in both experiments, the LIF signal equilibrated at the same level (see FIG. 6). The signal deviations of the raw data in both cases are less than 5% at the end points.

This example demonstrates how LIF can be used to examine of the blending kinetics of mixtures. It also verifies the consistency of the end point signals from mixtures having similar concentrations but different blending kinetics.

EXAMPLE 4

Usage of LIF to Measure End-Point Concentrations of Powder Mixtures

Blend homogeneity end-point concentration was determined at 50 rotations for triamterene powder concentration from 0.1% to 10% by weight. The end-point results are summarized in the table below. The relative standard deviation at the end-point (of 30 data points) for all these mixing experiments was less than 5%.

| Mixing End-Point | 10% T/L | 5% T/L | 1% T/L | 0.5% T/L | 0.1% T/L | 100% L |
|---|---|---|---|---|---|---|
| LIF Signal, Volts Average (70–100 rotations) | 12.25 | 8.58 | 3.29 | 2.25 | 1.34 | 0.96 |
| Std. Dev. | 0.30 | 0.29 | 0.12 | 0.07 | 0.05 | 0.01 |
| % RSD | 2.42 | 3.38 | 3.70 | 3.08 | 4.00 | 0.54 |

Figure 7:
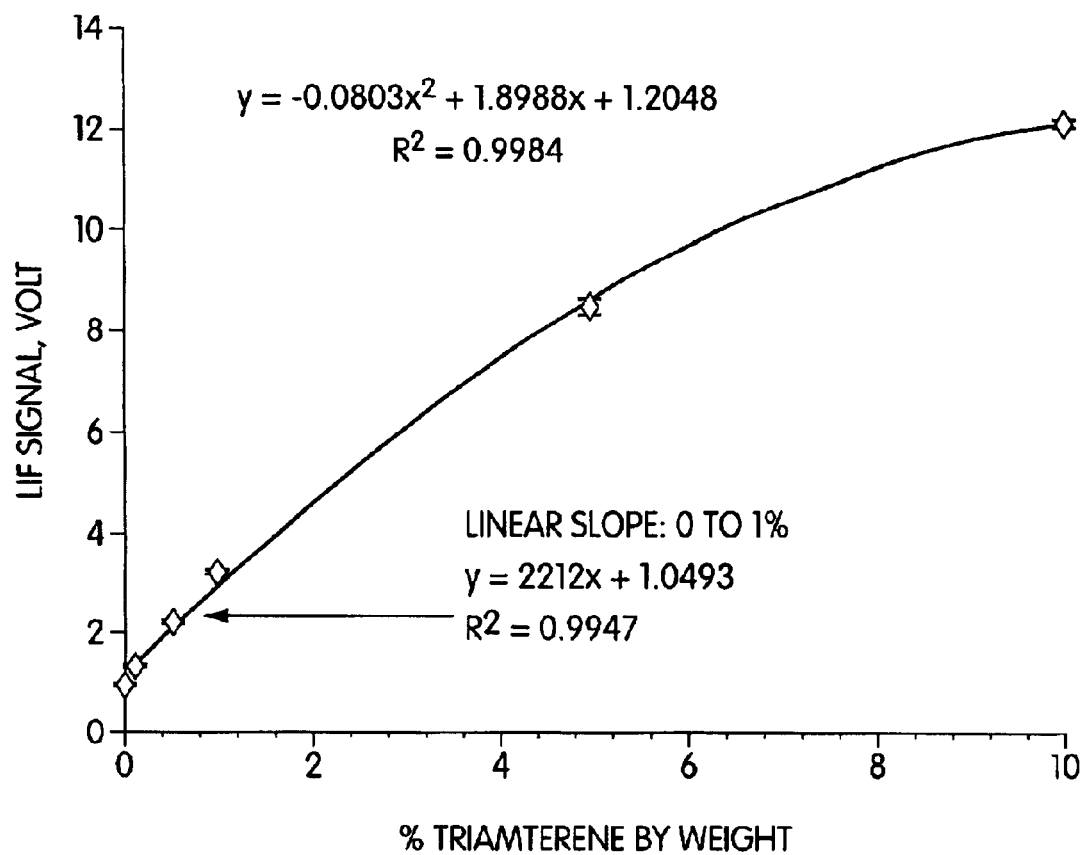
FIG. 7 graphically illustrates the correlation between LIF signal and triamterene concentration at mixing end points for the mixtures described in Example 4.

A correlation curve was generated with the data in the above table and was fitted by a polynomial equation with $R^2$ of 0.9984 (see FIG. 7). The curve can be used as a calibration curve for the instrument that provides triamterene concentration values from LIF signals under the conditions of the experiment. Linearity is observed at the lower concentration ranges from 0 to 1% triamterene with a linear equation of y=2.212x+1.0493 and an $R^2$ of 0.9947. It is believed that the non-linearity of the curve results from saturation of the PMT with the high fluorescence from the more concentrated samples. It is believed that the linearity of the slope can be extended further into the higher concentration range by lowering the power of the laser, by lowering the PMT voltage bias and by operating at a less sensitive excitation wavelength.

This example demonstrates the ability to measure end-point concentrations of a wide range of powder drug concentrations in a consistent and on-invasive manner. Furthermore, it demonstrates that LIF measurements may be used to correlate powder concentration of a particular drug in a mixture.

EXAMPLE 5

Comparison of LIF Analysis with Conventional Thief Sampling Analysis to Assess Blending Process Kinetics Blending studies were conducted in a 2.5 cubic foot bin blender. All powders were sieved before use. The rotation rate was set at 10 rpm. 300 g of triamterene was added to the bottom of a blender followed by another component, an excipient (6 kg anhydrous lactose with 6 g Carb-O-Sil) resulting in an actual concentration of 4.75% triamterene by total weight of mixture.

The excitation energy used by the LIF instrument was 460 nm with the PMT set at 305 volts bias. LIF readings were obtained continuously during each rotation of the blender, up to 70 rotations, except when the blender was stopped for thief sampling.

Figure 8:
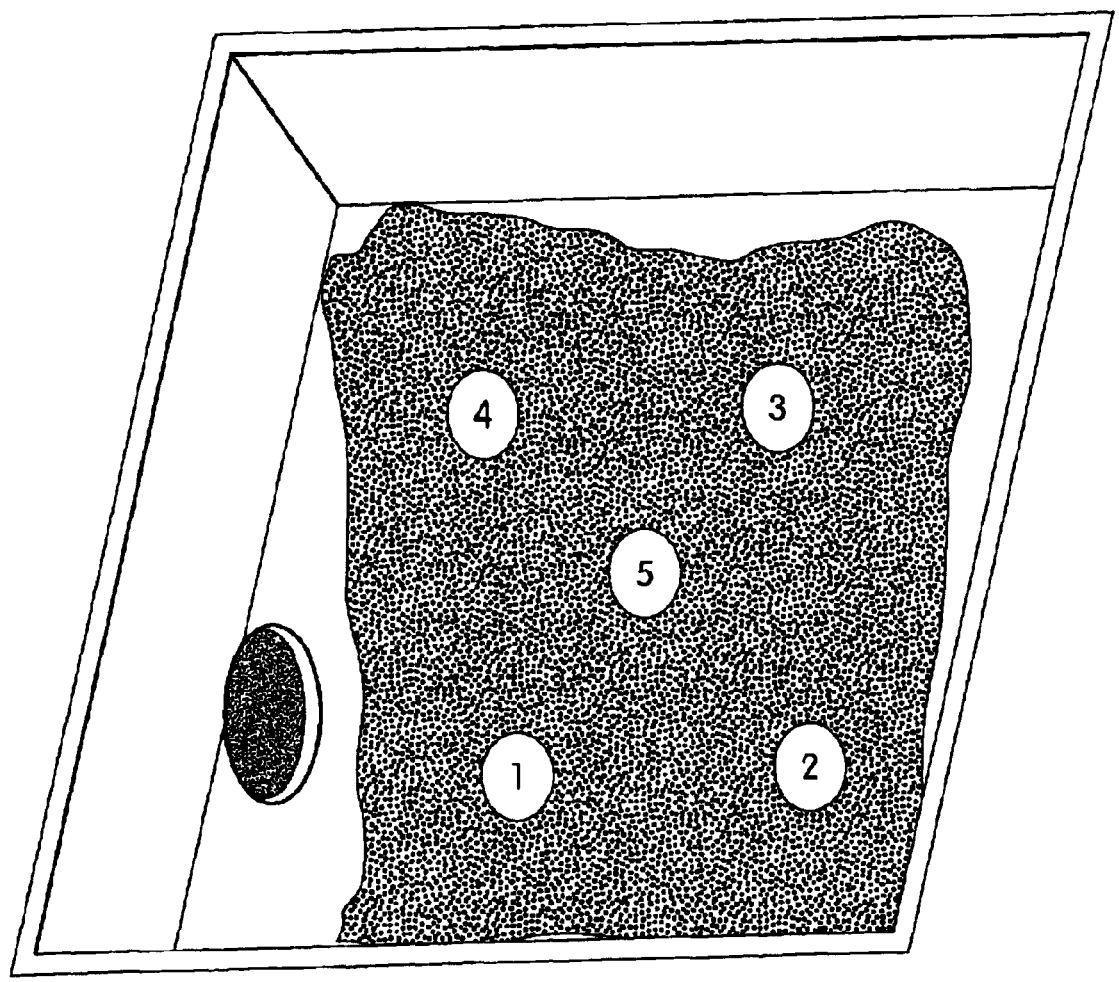
FIG. 8 schematically illustrates the thief sampling positions described in Example 5.

Thief samples were obtained periodically at the $5^{th}$, $10^{th}$, $30^{th}$, $50^{th}$ and $70^{th}$ rotations by collecting about 500 mg of thief sample the top of the blender at 5 designated positions labeled P1, P2, P3, P4 & P5 as shown in FIG. 8. The assay of thief samples was based on an adapted USP spectrophotometric protocol.

Figure 9:
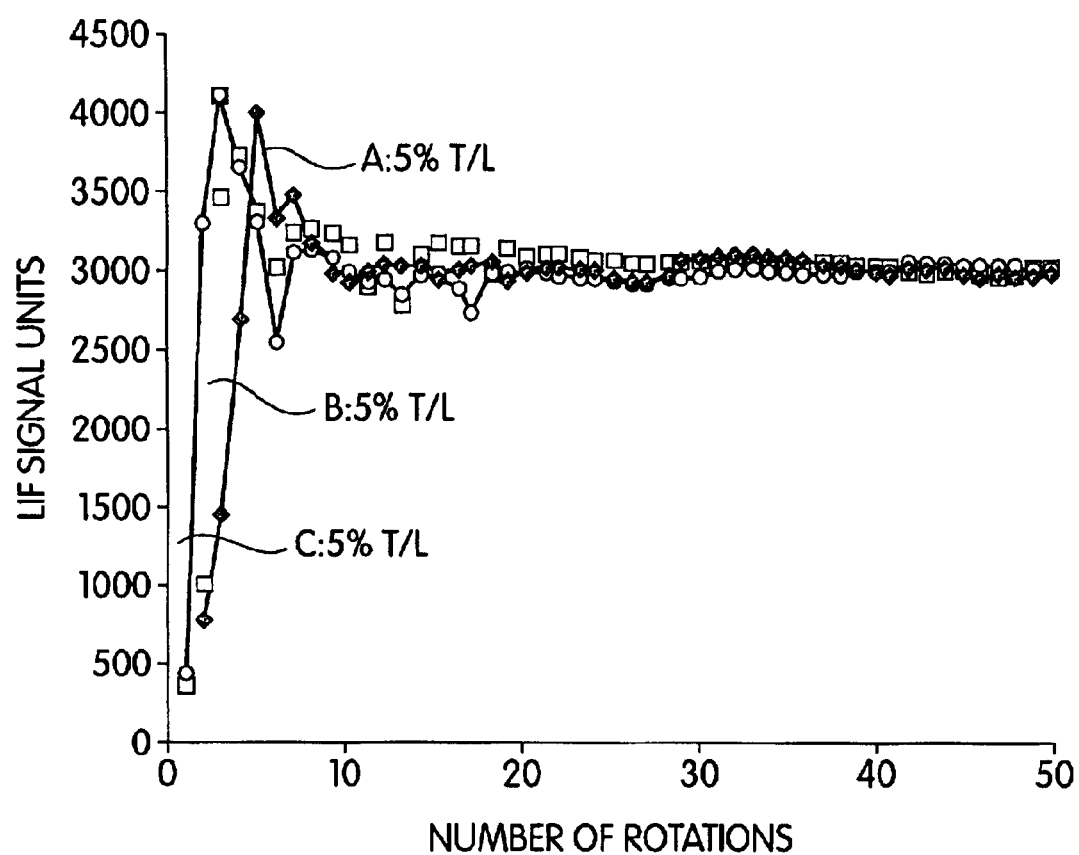
FIG. 9 shows blending profiles for three respective replicate runs as described in Example 5.

Three replicate blending runs (A, B, and C) were performed on this triamterene-lactose formulation. Mixing profiles generated from the LIF signals for the three runs are illustrated in FIG. 9. The kinetics of mixing over the first ten rotations is similar but not identical. This observation enhanced the notion that this real-time non-invasive technology is very sensitive to small changes in how the active ingredients are loaded into the bin blender which may have varied during the runs. Blend homogeneity is observed to be complete after 20 rotations.

The blend homogeneity end-point was determined based on the equilibrium steady state of the triplicate runs. Between rotations 20 to 30, the relative standard deviation is 1.51% (see Table 2). Further equilibrium of powder homogeneity is observed to 50 rotations that provided data that suggested sensitivities to further mixing generating data with 0.15% RSD.

TABLE 2

Homogeneity End-Point Determination

| Rot. No. | Run A | Run B | Run B | AVERAGE | STDEV | % RSD |
|---|---|---|---|---|---|---|
| Av. 20–30 | 2990.24 | 3021.97 | 2933.02 | 2981.74 | 45.08 | 1.51 |
| Av. 30–50 | 2984.21 | 2981.90 | 2975.63 | 2980.58 | 4.44 | 0.15 |

Figure 10:
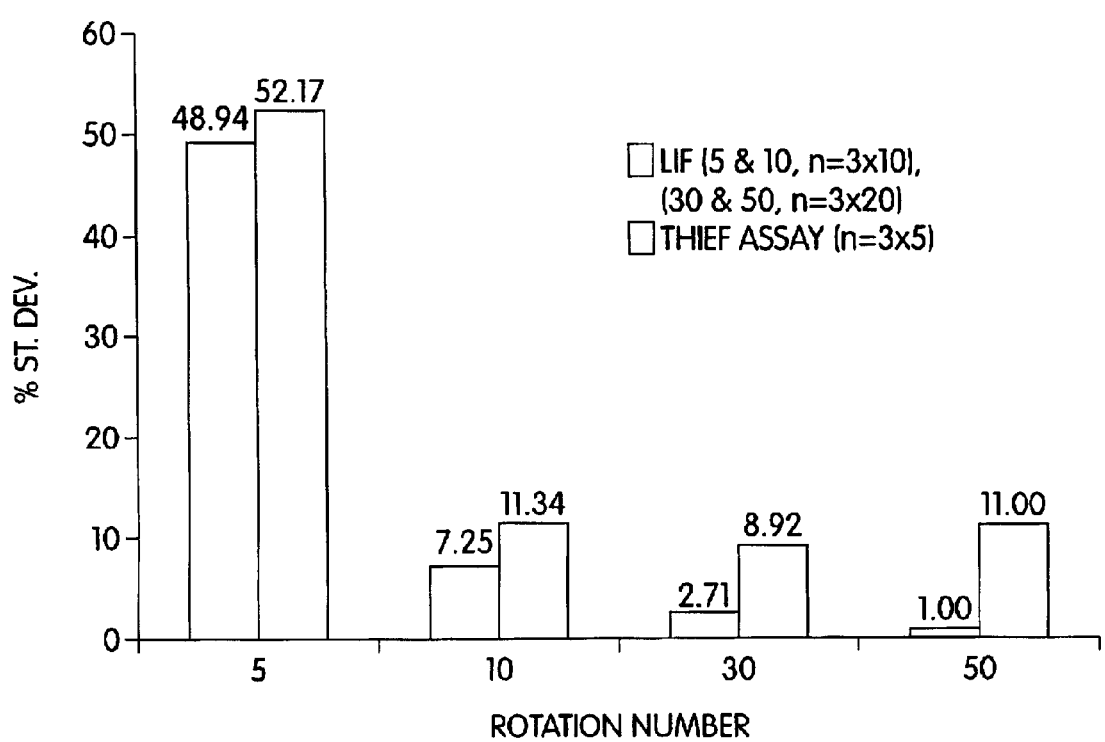
FIG. 10 graphically compares the standard deviation as a function of rotation number of the thief sampling data as compared to the LIF data as described in Example 5.

LIF readings were then compared to the results obtained from the thief samples (see FIG. 10). Both the LIF data and the thief sample data graph show the typical trend for powder blending starting with a high deviation and then settling down to a low deviation upon achieving blend homogeneity. Initial sampling at the $5^{th}$ rotation showed an unmixed chaotic state with large differences in standard deviations. As the powder mixtures in the blender begin to settle to a steady state at the $10^{th}$ rotation, the deviation decreased.

Thief sampling at end points after the $10^{th}$, $30^{th}$ and $50^{th}$ rotations cannot be resolved any better than between 9 to 11% respectively. By this account, the thieving data suggest that the blend homogeneity end-point was achieved after the $10^{th}$ rotation.

Continuous LIF measurements however suggested that mixing continued from the $10^{th}$ rotation (stdev @ 7.25%) through to the $50^{th}$ rotation (stdev @ 1.00%). The decreasing variance of the triplicate runs at the $30^{th}$ rotation (stdev @ 2.7%) supported this claim. Further refinement in mixing can be observed by mixing to 50 rotations achieving a variance of 1%.

This example illustrates the ability of LIF analysis to provide a comparable and possibly more accurate method of analyzing the uniformity of a mixture than a conventional thief sampling technique.

EXAMPLE 6

Usage of LIF Instrument to Determine Blending Endpoint Concentrations

In this set of experiments, triamterene (the active ingredient) was loaded at three different positions in a blender. The resulting mixture in each experiment included an actual concentration of triamterene of 4.75% by weight with the remainder being lactose. In the first run, triamterene was loaded at bottom. In the second run, triamterene was loaded in the middle. In the third run, triamterene was loaded at the top of the blender. The purpose of the experiment was to examine the sensitivity of the LIF instrument, which had access to the mixture through a window positioned near the top of the blender, in determining different mixing kinetic profiles. The results are shown in FIG. 11.

The mixing kinetic profiles for the three runs were observed to be different from each other for the first 10 rotations. These results suggest sensitivity to how the active ingredient is initially loaded into the blender. In the experiment in which triamterene was placed at the bottom of the blender, the initial LIF signal from the first rotation was low because triamterene was not detected by the instrument. As mixing progresses, triamterene detected by the instrument increased and gradually equilibrated at the end-point. When loading occurred at the middle of the blender, there was a gradual drop in LIF signal from high to the equilibrium end-point. When loading occurred at the top, a saturating LIF signal was observed for several rotations before gradually dropping off to equilibrium.

Figure 11:
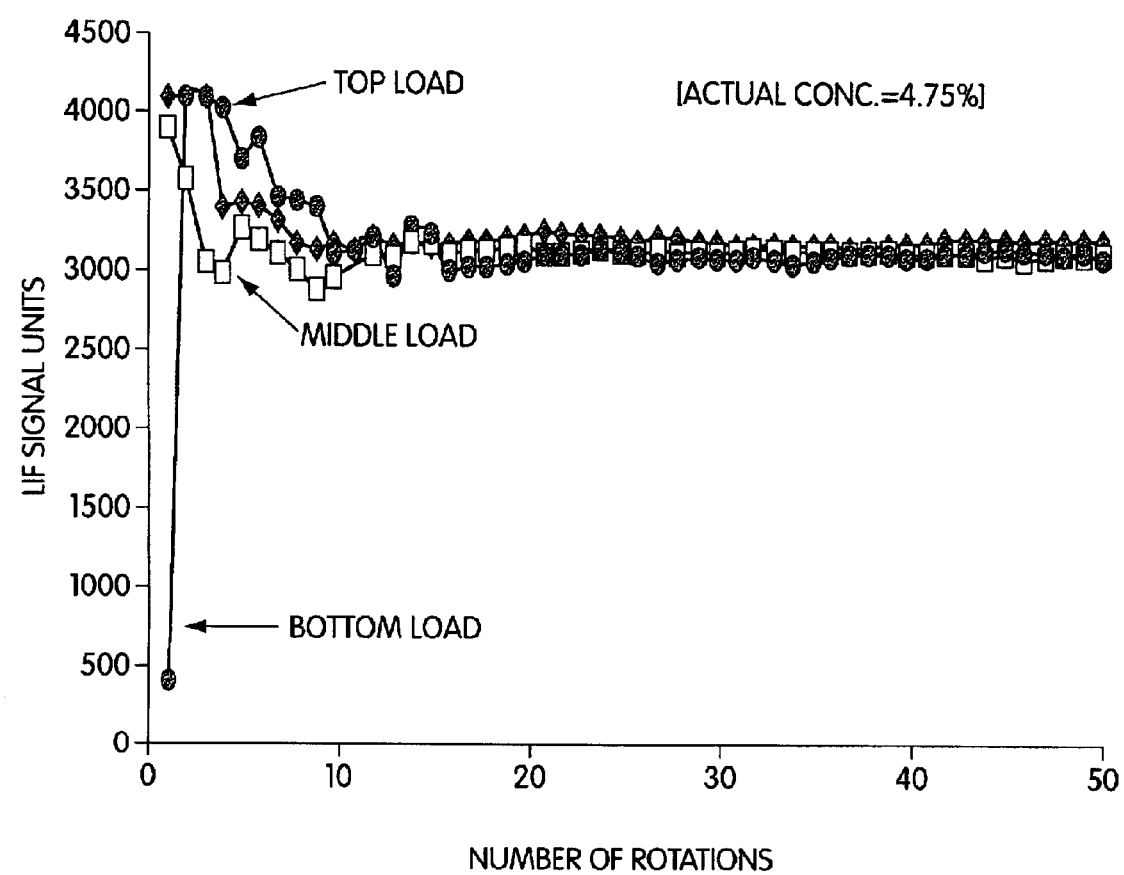
FIG. 11 shows mixing profiles for mixtures loaded at different positions in the blender as described in Example 6.

All three runs, irrespective of the positions to which the active is loaded, equilibrated at the same blending end-point with deviations from each other in the order of 2.2%, as illustrated in FIG. 11 and in the following table. In this set of experiments, as in the previous cases described in Example 5, blend homogeneity was observed from after approximately 20 rotations. Further refinement of end-point resolution is observed by mixing to 50 rotations.

TABLE 3

| | Homogeneity End-point | | | | | |
|---|---|---|---|---|---|---|
| Rot. No. | Top Load | Middle Load | Bottom Load | Average | STDEV | % RSD |
| 20–30 | 3224.78 | 3117.33 | 3095.20 | 3145.77 | 69.32 | 2.20 |
| 30–50 | 3191.18 | 3116.59 | 3103.65 | 3137.14 | 47.25 | 1.51 |

Figure 12:
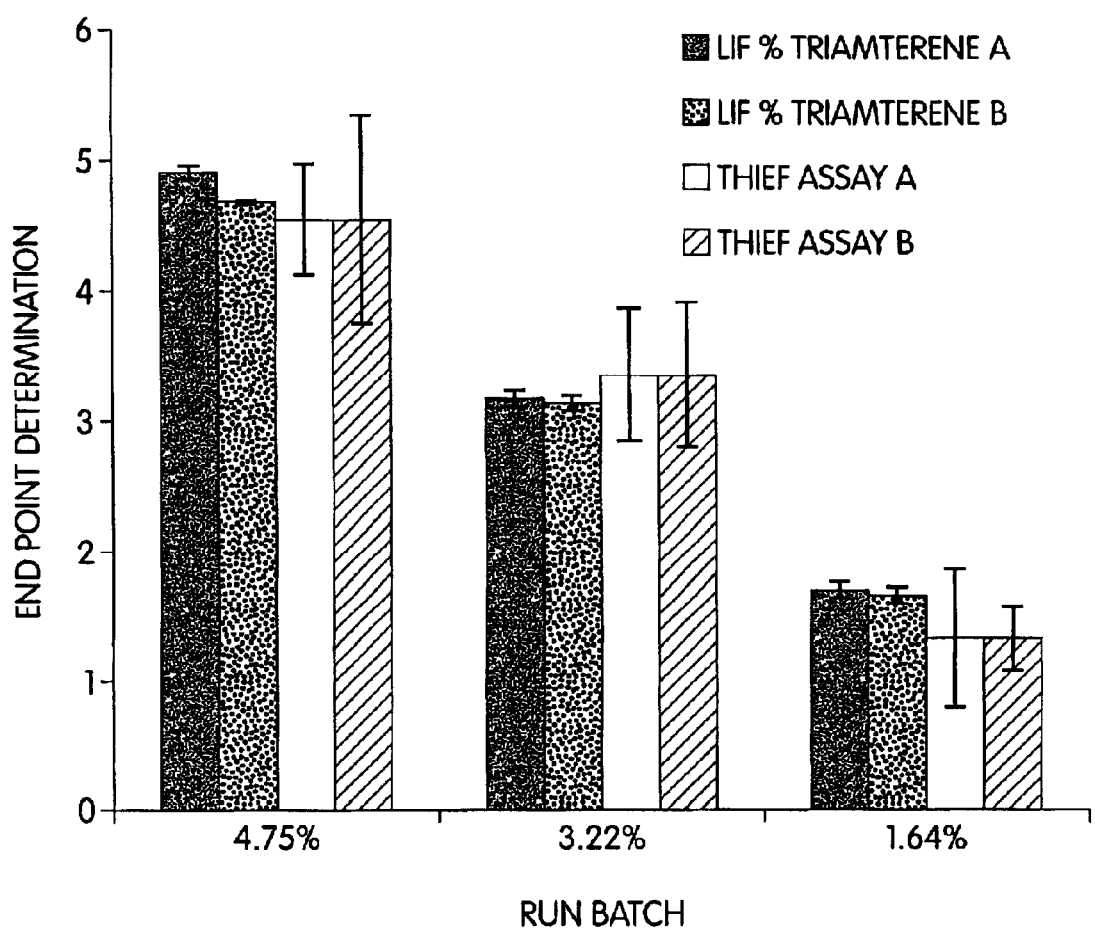
FIG. 12 graphically compares the end point determination from LIF measurements to thief sampling measurements as described in Example 6.

Additional experimentation was performed to compare LIF technique to the conventional thief sampling technique described in Example 5. Following the above procedure, mixtures including 3.22% and 1.64% triamterene by weight were prepared and loaded into the top, middle, and bottom of the blender in successive experiments. The mixtures were analyzed using the LIF technique and the thief sampling technique described in Example 5. A mixture of 4.75% triamterene by weight was also loaded into the top, middle, and bottom of the blender in successive experiments and analyzed using the thief sampling technique. The results obtained from the top (A) and the bottom (B) for the two techniques are illustrated graphically in FIG. 12.

The LIF results were validated closely with the LIF end-point data with the exception that thief sampling had much larger deviation as indicated by standard deviation bars on the graph. The large deviations incurred with thief sampling are as expected and consistent with published reports elsewhere.

This example also established that LIF analysis provides more consistent results than thief sampling. In addition, the example shows the sensitivity of LIF data early in the blending process to the position of the instrument in relation to the loading position of the active ingredient. However, the example establishes that regardless of the loading position, the same end point is reached for equivalent mixture concentrations.

EXAMPLE 7

LIF Measurement at Multiple Locations to Monitor Uniformity of a Mixture

A 5% triamterene in lactose mixture was used. The drug (triamterene) was added at the bottom of a tube blender followed by the addition of lactose as the excipient. The blender was filled to about a 50% fill-volume. The blender was then tumbled as shown in FIG. 13.

Figure 13:
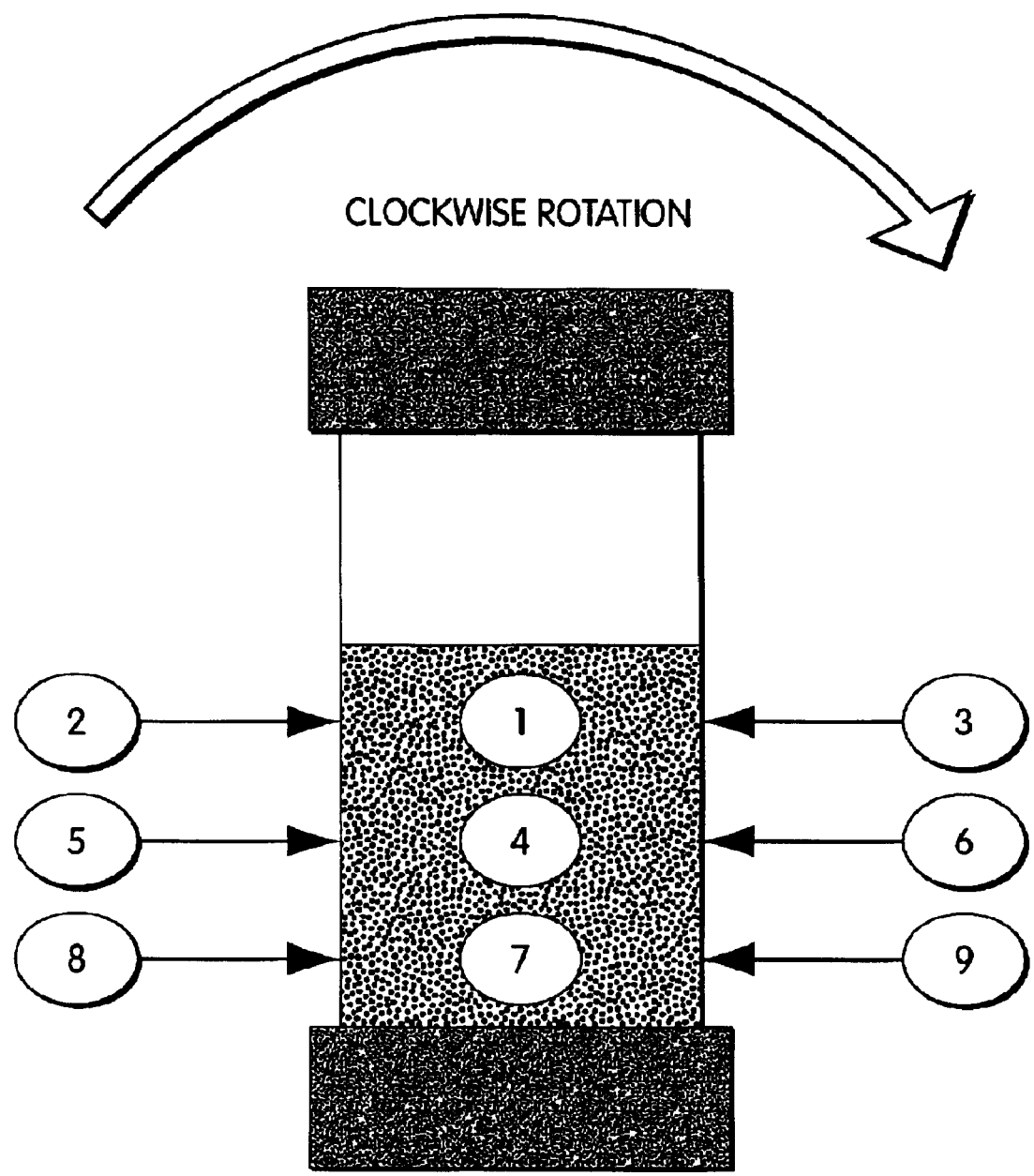
FIG. 13 schematically illustrates a tube tumbler including the nine locations of LIF data acquisition as described in Example 7.

After each rotation, LIF data was acquired non-invasively from the 9 specific positions as shown in FIG. 13 by moving a fiber optic probe to the different positions. This design simulated 9 points of fiber optic data acquisition on the tube blender. The 3 sets of positions were located at 120° angle from each other around the circumference of the blender.

Figure 14A:
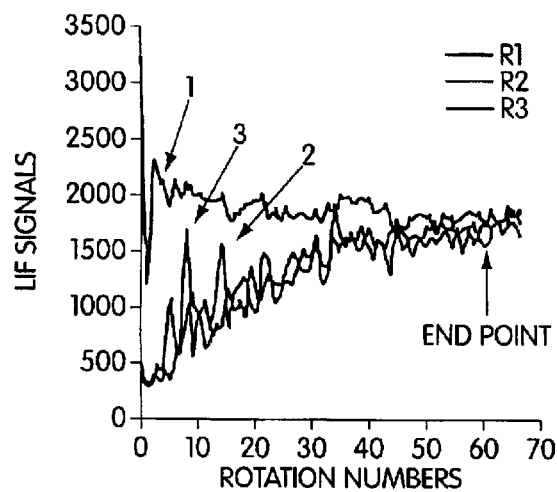
FIG. 14A shows mixing profiles obtained at locations 1–3 for the mixture described in Example 7.
Figure 14B:
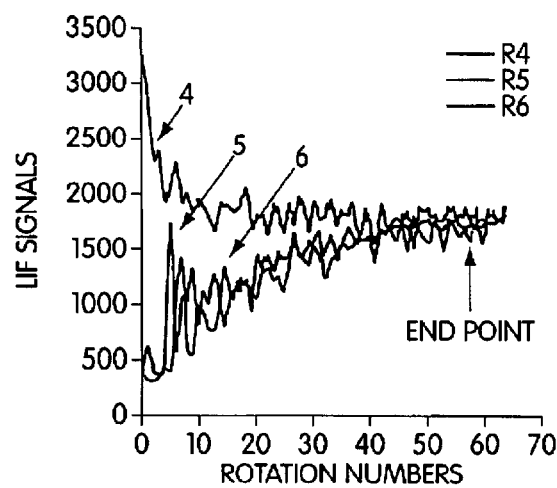
FIG. 14B shows mixing profiles obtained at locations 4–6 for the mixture described in Example 7.
Figure 14C:
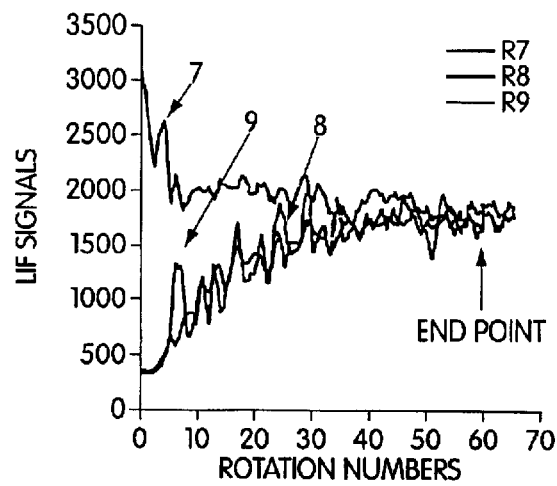
FIG. 14C shows mixing profiles obtained at locations 7–9 for the mixture described in Example 7.

The mixing profiles at the 9 different locations are shown in FIGS. 14A–14C. The initial chaotic states of mixing were demonstrated at all 9 positions followed by an equilibration at homogeneity end point. Each of the 9 positions monitored came to the same equilibrium point. The results imply that it may suffice to monitor homogeneity end point using only one LIF instrument at one selected position for a blender of this size.

The results illustrate an embodiment which uses LIF measurements at different positions in the blender to simulate the use of multiple LIF probes. The results establish the consistency of the end point concentrations determined at the different positions. Furthermore, the example demonstrates that the spatial variation can be measured under dynamic conditions.

EXAMPLE 8

Usage of LIF to Determine Uniformity of a Semi-Solid Mixture

Figure 15:
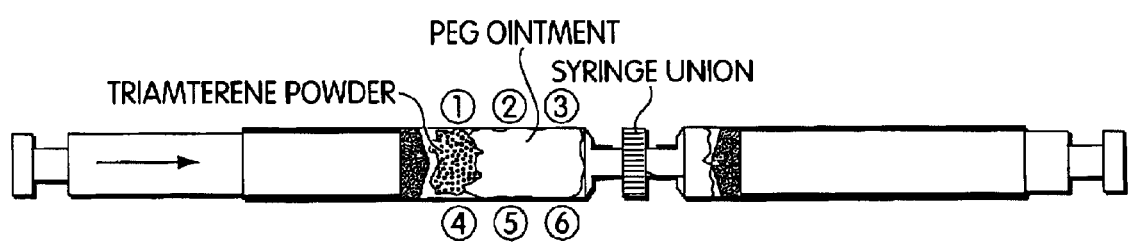
FIG. 15 schematically illustrates a two-syringe mixing chamber including the six locations of LIF data acquisition for the semi-solid mixture described in Example 8.

PEG ointment, a base excipient, was mixed with triamterene, a drug component, to produce a semi-solid pharmaceutical mixture. A series of mixtures having triamterene concentrations ranging from 0.5 to 2.0% by weight. Mixing was conducted in a two-syringe mixing chamber and LIF signals were measured non-invasively and in real-time through the glass syringe wall at six different locations as shown in FIG. 15.

Figure 16A:
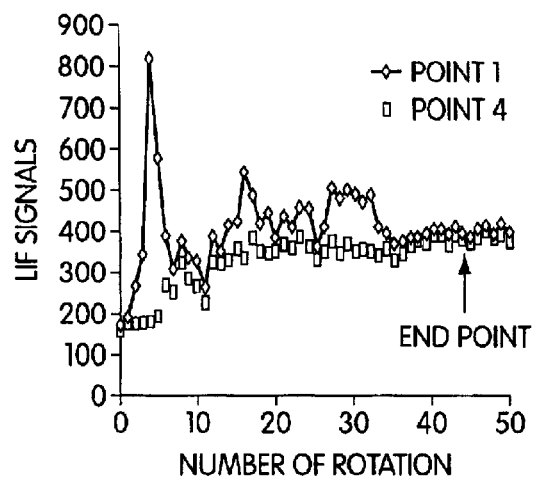
FIG. 16A shows mixing profiles obtained at locations 1 and 4 for the mixture described in Example 8.
Figure 16B:
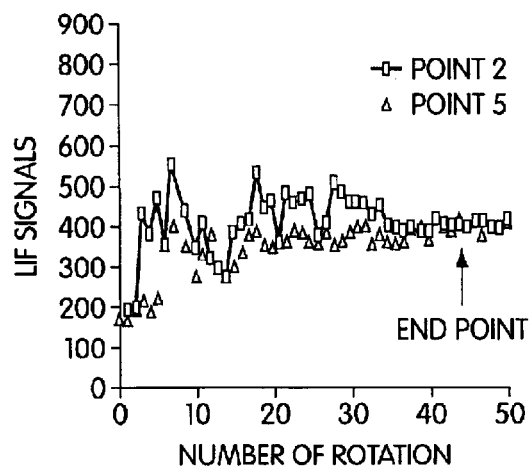
FIG. 16B shows mixing profiles obtained at locations 2 and 5 for the mixture described in Example 8.
Figure 16C:
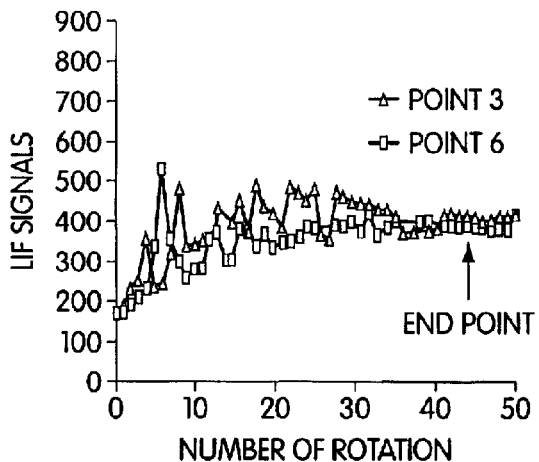
FIG. 16C shows mixing profiles obtained at locations 3 and 6 for the mixture described in Example 8.

The mixing profiles obtained by measuring LIF signals at the six locations are illustrated in FIGS. 16A–16C. The data shows large variations in the LIF signals for the different positions at low numbers of rotation. As the number of rotations increased, however, the LIF signals at all of the positions approached a constant value. The results show the sensitivity of LIF data early in the blending process to instrument position, but establish that the same end point is reached regardless of the instrument position.

Figure 17:
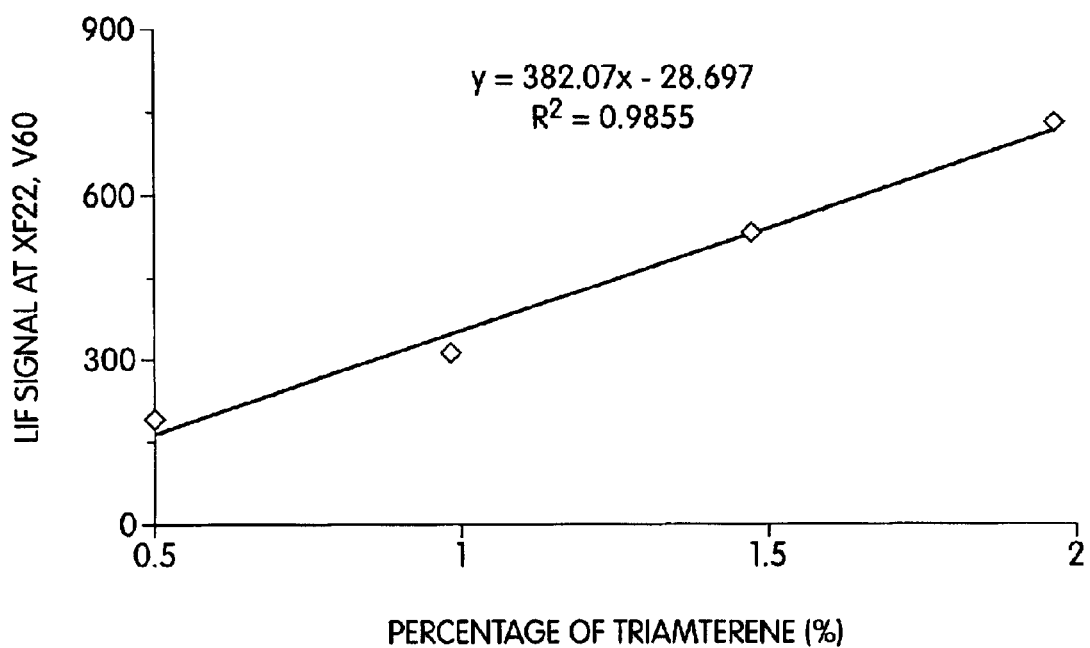
FIG. 17 graphically illustrates the correlation between the percentage of triamterene and LIF signal for the mixture described in Example 8.

A linear correlation between drug concentration and LIF signal was established and shown in FIG. 17.

This example establishes the ability of LIF to monitor the uniformity of a semi-sold mixture non-invasively and in real-time until the blend homogeneity end-point is reached.

EXAMPLE 9

Usage of LIF Instrument to Monitor Tablet Uniformity

Figure 18:
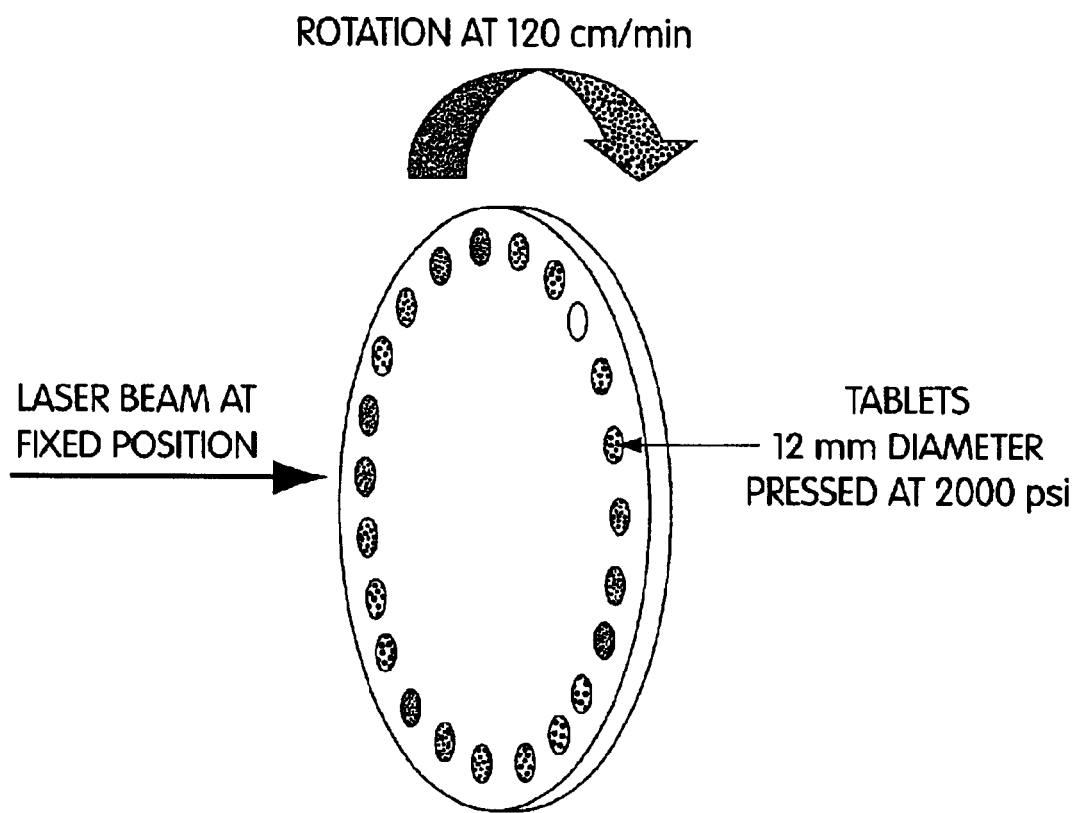
FIG. 18 schematically illustrates the setup for analyzing pharmaceutical tablets as described in Example 9.

A series of homogeneous powder mixtures (~300 mg) having respective drug component concentrations of 0.1%, 0.5%, 1%, 5%, and 10% by weight of total mixture were prepared. The mixtures were placed in a 20 mm square tablet holder with a 12 mm diameter chamber and pressed using a Carver hydraulic press at 2000 psi to form tablets. These tablets were then attached to a rotating disc to simulate the monitoring of tablets moving on a production line, for example on a tablet handling apparatus, at the speed of 120 cm/minute (see FIG. 18). Individual tablets were monitored with LIF at a fix location as the tablet moved past the continuous beam of light.

Figure 19:
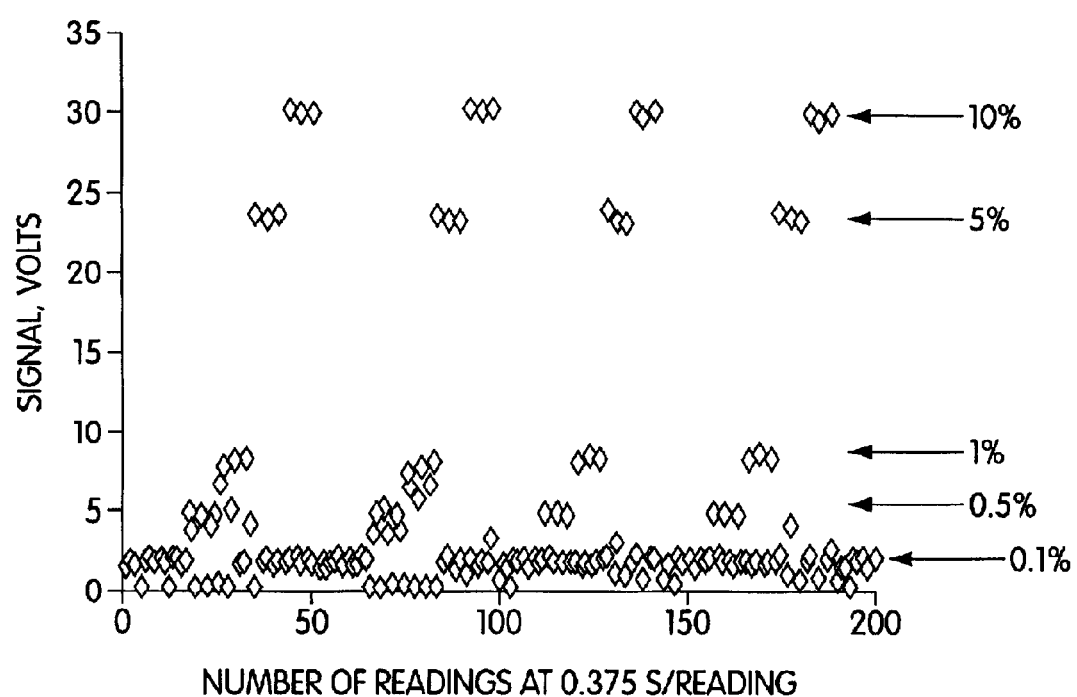
FIG. 19 schematically illustrates the LIF signal for tablets at various concentrations of triamterene as described in Example 9.
Figure 20:
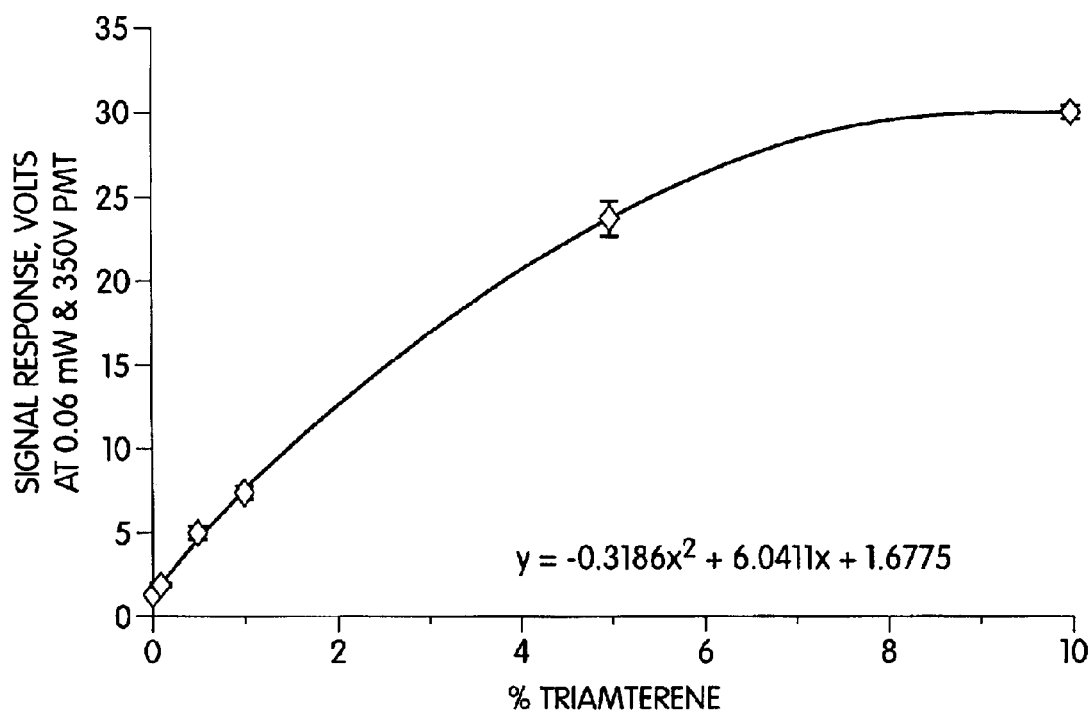
FIG. 20 graphically illustrates the correlation between LIF signal and percentage of triamterene as described in Example 9.

LIF data resulting from data acquired from the individual tablet surfaces were graphed as shown in FIG. 19 showing the different signals obtained from different drug concentrations. The correlation of LIF signals with drug concentration in the tablet was established and shown in FIG. 20.

Figure 21:
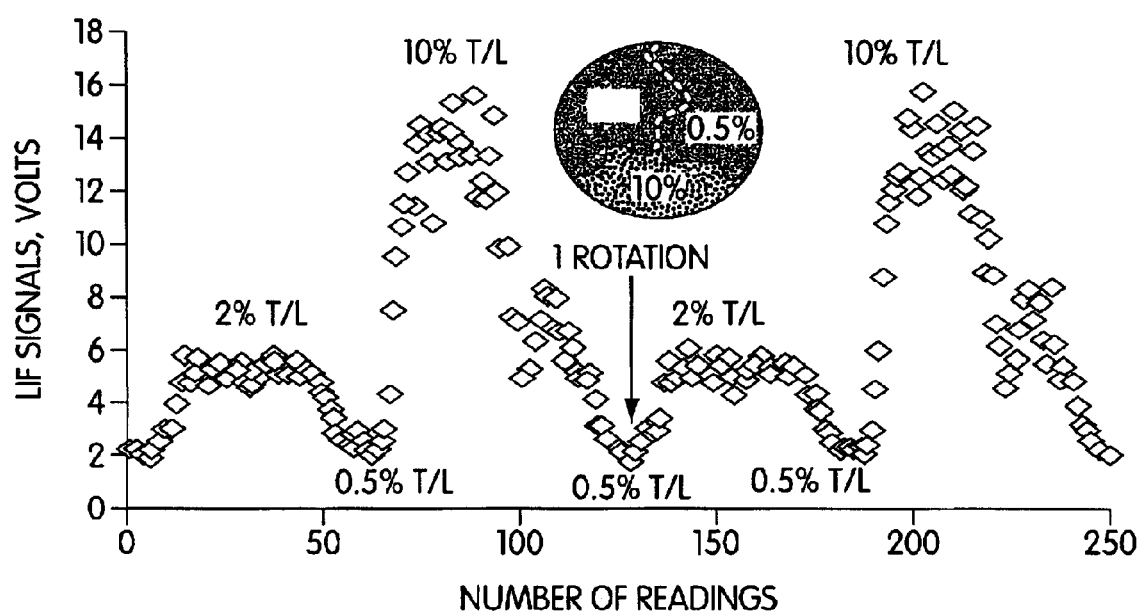
FIG. 21 graphically illustrates the LIF signal obtained at different locations on the surface of an inhomogeneous tablet as described in Example 9.

In another series of experiments, LIF was utilized to scan tablet surfaces for recognition of non-uniformity. In these experiments, a tablet having a non-uniform composition were prepared by pressing three separate powders at concentrations of 0.5%, 2% and 10% triamterene. LIF was used to scan the tablet in a circular motion around the circumference of the tablet. The resultant data shown in FIG. 21 illustrates the different concentrations of triamterene at different positions on the tablet surface.

This example shows the use of an LIF instrument to perform concentration and uniformity measurements for tablets.

EXAMPLE 10

Usage of LIF Instrument to Monitor Powder Uniformity During Transport

Figure 22:
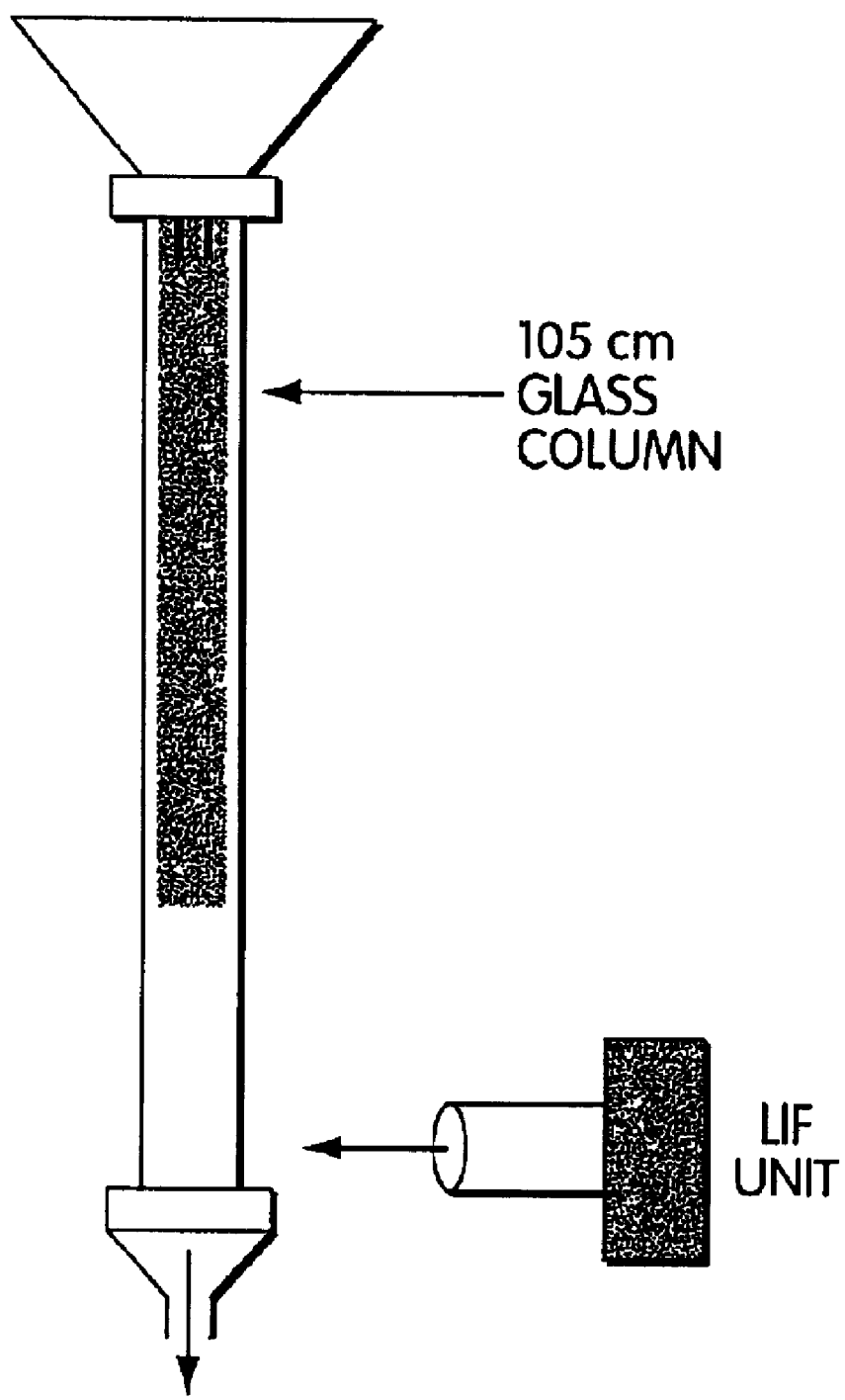
FIG. 22 schematically illustrates a powder discharge apparatus including an LIF instrument as described in Example 10.

A series of samples were prepared which included a homogeneous powder mixture comprising a formulation of 5% triamterene in anhydrous lactose was discharged through a glass column to simulate the transport of a mixture, for example, as done during processing. The column measured 5 cm in diameter and 105 cm in height. The content and powder concentration of the mixture was monitored at the bottom of the column using an LIF instrument (FIG. 22). The powder discharged at a flow rate of 170 g/min which translated into a linear flow rate of 55 cm/min.

Figure 23:
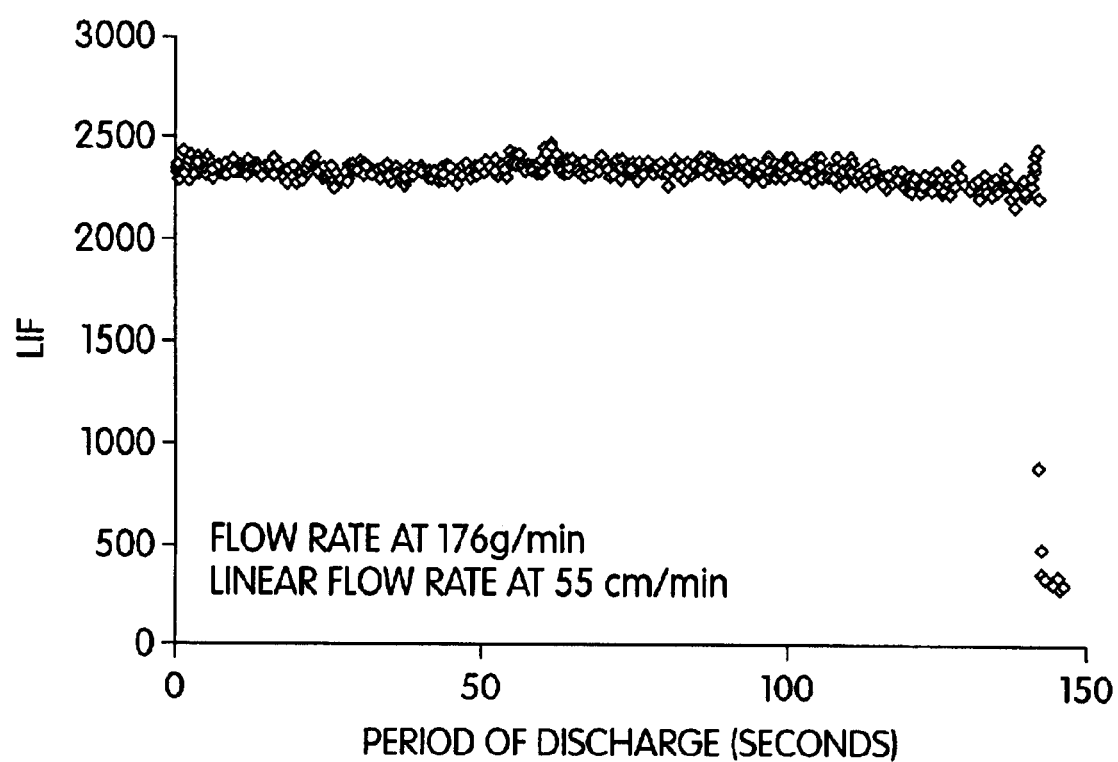
FIG. 23 graphically illustrates LIF signal as a function of time during the discharge of a homogeneous mixture of triamterene/lactose as described in Example 10.

The LIF data collected is shown in FIG. 23. A consistent LIF signal representative of the triamterene concentration were obtained by analyzing the homogeneous powder during discharge.

Using the same equipment as described above, another experiment which monitored the concentration of inhomogeneous powder mixture. To prepare the mixture, the outlet of the column was blocked and a series of powders having varying triamterene concentrations (0%, 0.1%, 1.0%, 5.0% and 10% by weight of mixture) in anhydrous lactose were respectively added to the column and stacked from the bottom upwards. The outlet of the column was opened to permit the discharge of the inhomogeneous mixture and LIF data was collected.

Figure 24:
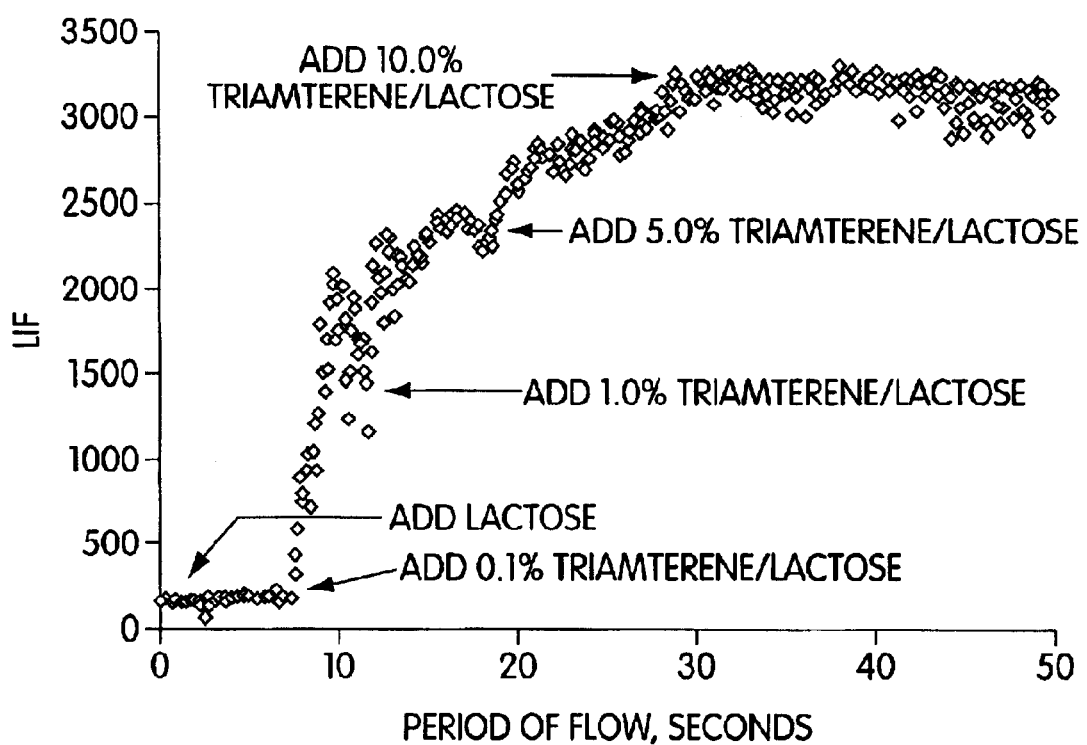
FIG. 24 schematically illustrates LIF signal as a function of time during the discharge of a non-homogeneous mixture of triamterene/lactose as described in Example 10.

The results obtained from the LIF analysis are illustrated in FIG. 24. The results show the increasing LIF signal as increasing concentrations of triamterene flowed past the LIF instrument. The total results of the experiment demonstrated a distinct discrimination between the different layers of powders of increasing drug concentrations as they were being discharged.

This example illustrates the usage of LIF to monitor component concentration and the uniformity of powders mixtures as the mixture during transport, for example, when being discharged from one unit operation to another.

EXAMPLE 11

Usage of LIF For Assessing Cleaning Processes

Figure 25:
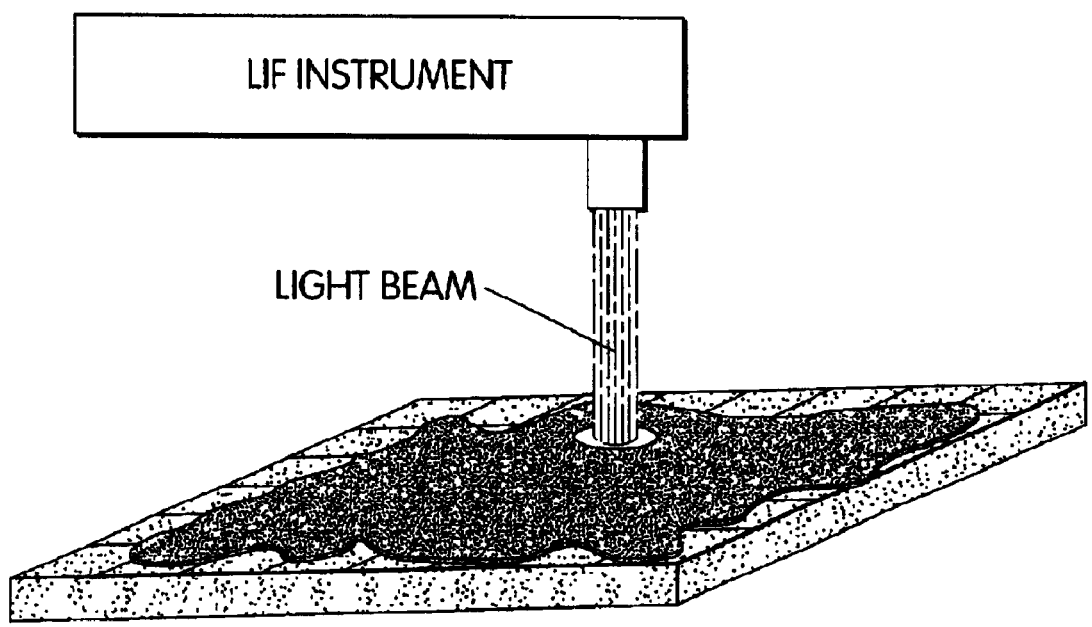
FIG. 25 schematically illustrates an LIF instrument used to analyze concentration on a surface as described in Example 11.

A quantitative amount (about 10.6 $g/cm^2$) of triamterene was dispersed on a 4 cm×4 cm stainless steel plate to simulate residual powder remaining, for example, on an interior surface of a processing apparatus (e.g., a blender) after processing. It is desirable for such residual powder to be cleaned from the processing apparatus so that the powder does not contaminate future processing. An LIF probe was used to scan the plate to determine the concentration of the residual powder at different points on the surface of the plate as shown schematically in FIG. 25. Then, the plate was sprayed with a wash solvent (1 mL 10% formic acid) and wiped with a kimwipe tissue to simulate a cleaning process. After cleaning, the LIF analysis was repeated using the same procedure.

Figure 26A:
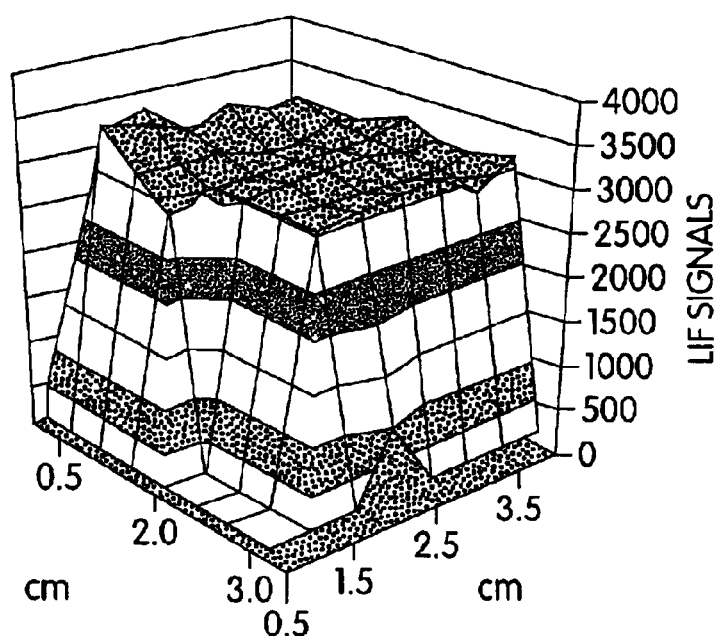
FIGS. 26A and 26B are surface images of the concentration of triamterene before and after cleaning, respectively, as described in Example 11.
Figure 26B:
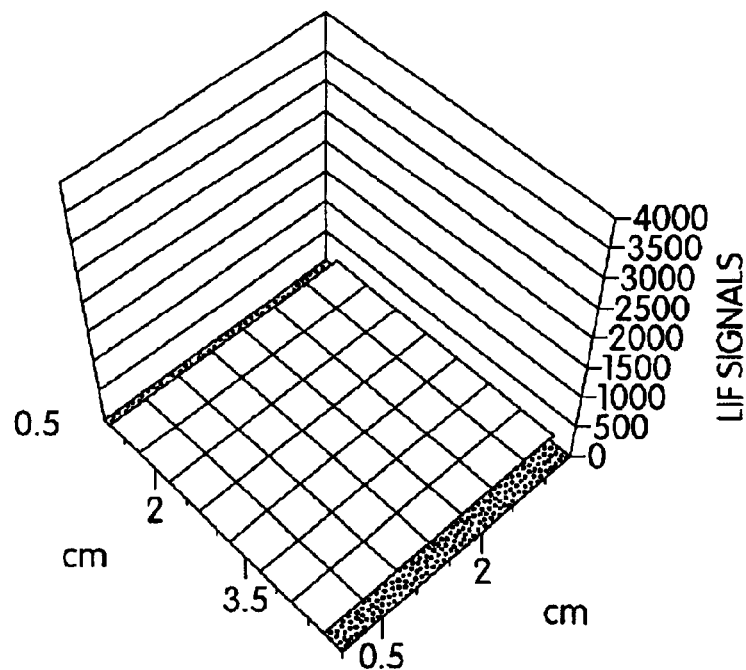

The results of the LIF analysis before and after cleaning are shown respectively as surfaces images in FIGS. 26A and 26B. Comparison of FIG. 26A to FIG. 26B illustrates the reduction in triamterene concentration on the plate surface by the cleaning process. Thus, the cleaning process was effective.

This example illustrates the ability of LIF analysis to assess the effectiveness of cleaning processes by generating surface images of concentration of a mixture component (e.g., a drug).

EXAMPLE 12

Usage of LIF To Assess Mixture Stability During Blending

Respective mixtures were prepared which included the same active pharmaceutical ingredient (particle size of about 200 $\mu$m and a bulk density of about 0.3 $g/cm^3$) mixed with different excipients. The excipient of the first mixture was lactose having a particle size of about 100 $\mu$m and a bulk density of about 0.62 $g/cm^3$. The excipient of the second mixture was Avicel (PH200) having a particle size of about 200 $\mu$m and a bulk density of about 0.2 $g/cm^3$. The excipient of the third mixture was Avicel (CP102) having a particle size of about 170 $\mu$m and a bulk density of about 0.87 $g/cm^3$.

In separate processes, the mixtures were mixed in a V-blender. LIF data was acquired during each process through a quartz window at the bottom of the blender. One data point was collected after each rotation and the mixtures were mixed for 100 rotations. For each process, equilibrium was established after about 35 rotations. LIF data from the remaining rotations (e.g. after equilibrium had been reached) provided an assessment of mixture stability. After each mixing process, the powder mixtures were divided into 10 samples and conventional HPLC analysis was done to provide comparative mixture stability data.

Figure 27A:
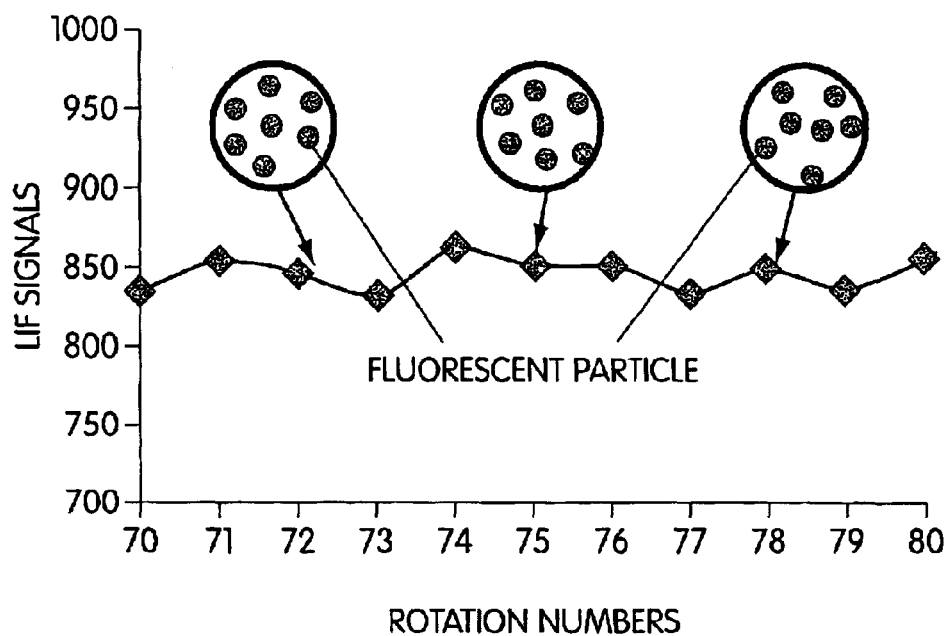
FIGS. 27A and 27B are schematic blending profiles of a relatively stable mixture and a relatively unstable mixture, respectively, as described in Example 12.
Figure 27B:
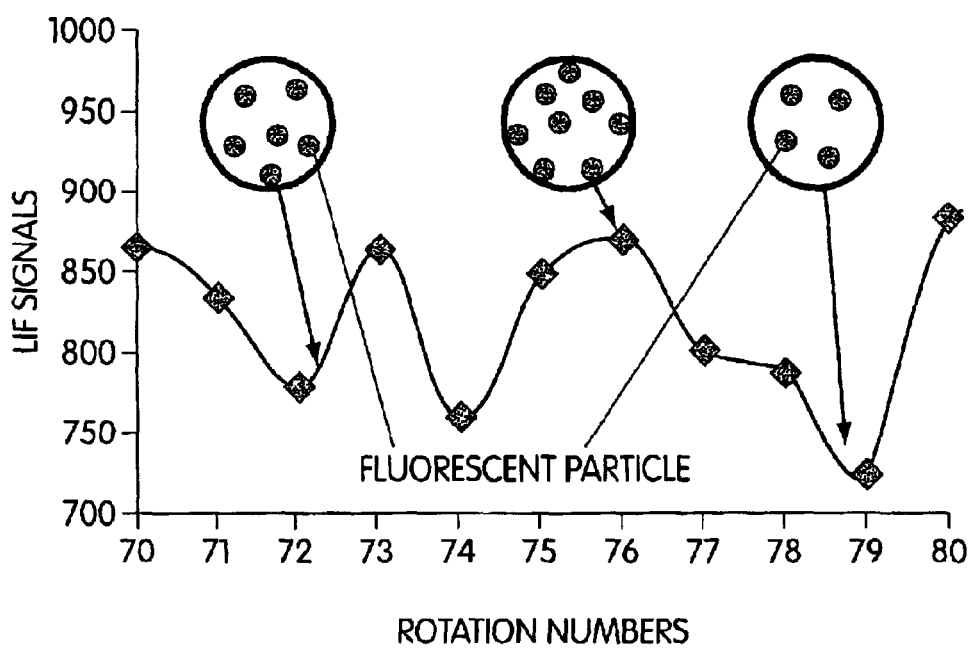

Mixture stability is a measure of the degree of deviation at equilibrium (steady state) conditions. FIG. 27A shows a relatively stable mixture having a small degree of deviation at equilibrium. FIG. 27B shows a relatively unstable mixture having a large degree of deviation at equilibrium conditions. Assessment of mixture stability provides a prediction regarding the degree of desegregation. Unstable mixtures are more likely to be desegregated which can impair the production of a uniform product. Desegregation of an unstable powder mixture can occur due to particle movement during, for example, transporting the mixture, discharging the mixture for storage, tableting, amongst other processes.

Figure 28:
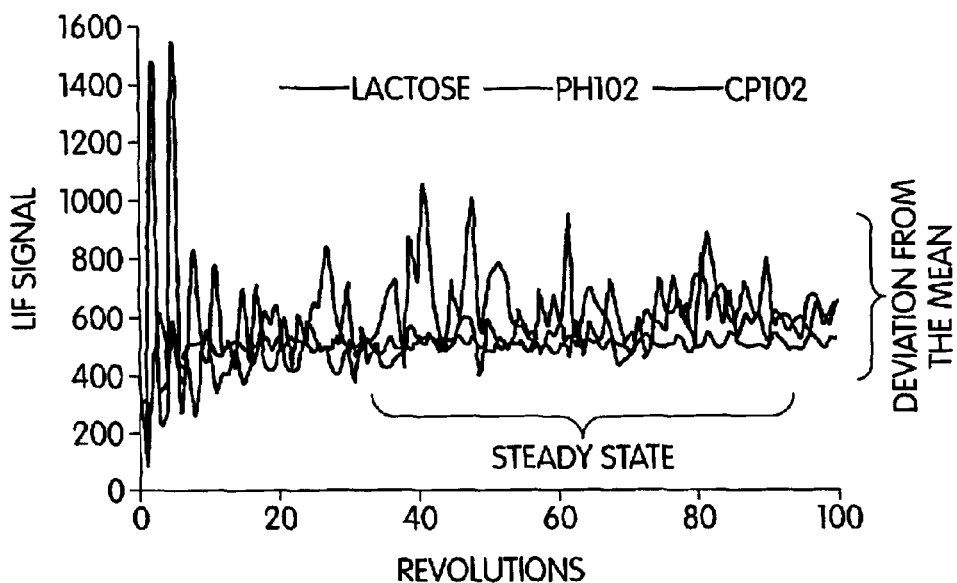
FIG. 28 shows blending profiles of the mixtures in Example 12.
Figure 29:
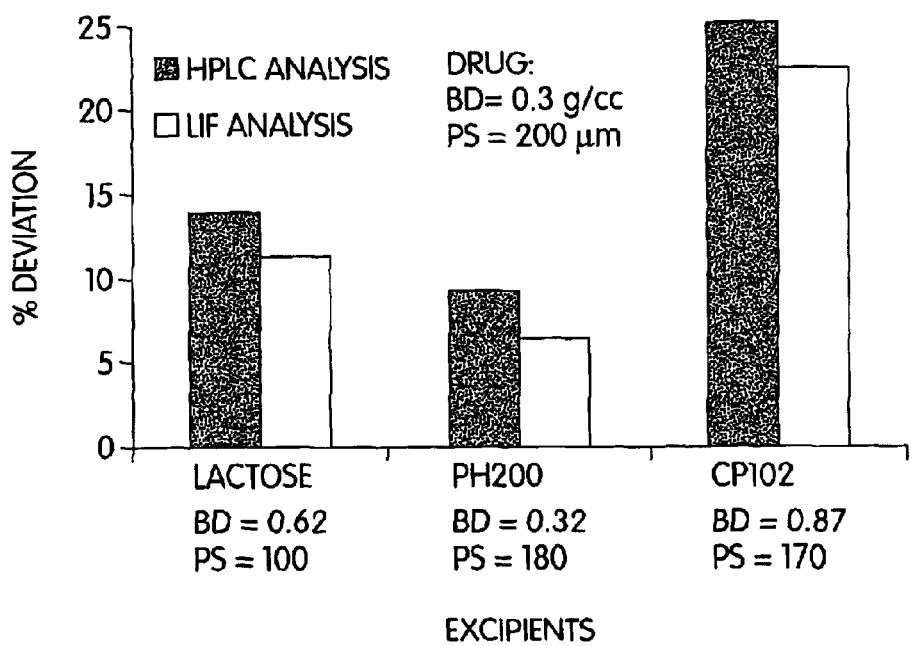
FIG. 29 shows the average percentage deviation at equilibrium of the mixtures in Example 12 as measured by LIF and as measured using HPLC.

The blending profiles of the three mixtures obtained by the LIF analysis are shown in FIG. 28. FIG. 29 shows the average percentage deviation at equilibrium (steady state) for the three mixtures. As shown in FIG. 29, the LIF data is in close agreement with data obtained from the HPLC analysis. The results indicate that mixture stability increased (i.e., percentage deviation decreased) as the excipient particle characteristics (e.g., particle size and bulk density) became more similar to the active ingredient particle characteristics.

This example illustrates the ability of LIF to assess mixture stability during mixing which provides a prediction regarding the degree of desegregation.

Those skilled in the art would readily appreciate that all parameters listed in the above specification including examples are meant to be exemplary and that actual parameters will depend upon the specific application for which the methods and systems of the present invention are used. It is, therefore, to be understood that the foregoing embodiments are presented by way of example only and that, within the scope of the appended claims and equivalents thereto, the invention may be practiced otherwise than as specifically described.

What is claimed:

1. A system for processing materials comprising:
   a processing apparatus configured to process a mixture of more than one component;
   a fluorescence instrument operatively associated with the processing apparatus capable of measuring the uniformity of the mixture during processing of the mixture; and
   an RF converter capable of converting voltages received from the fluorescence instrument to an RF signal.

2. The system of claim 1, wherein the processing apparatus is constructed to process a mixture of pharmaceutical components.

3. The system of claim 1, wherein the processing apparatus comprises a mixing apparatus.

4. The system of claim 1, wherein the processing apparatus comprises an apparatus constructed to transport the mixture.

5. The system of claim 1, wherein the processing apparatus comprises a tablet-handling apparatus.

6. The system of claim 1, wherein the processing apparatus comprises a storage unit.

7. The system of claim 1, wherein the fluorescence instrument is mountable on the exterior of the processing apparatus.

8. The system of claim 1, wherein the fluorescence instrument includes a fiber-optic probe insertable within a processing space of the processing apparatus.

9. The system of claim 1, wherein the fluorescence instrument includes a laser.

10. The system of claim 1, wherein the fluorescence instrument includes a light source capable of emitting light over a range of wavelengths.

11. The system of claim 1, wherein the fluorescence instrument is capable of measuring the uniformity of the mixture in real-time during processing of the mixture.

12. The system of claim 1, wherein the fluorescence instrument is capable of measuring the uniformity of the mixture on-line during processing of the mixture.

13. The system of claim 1, wherein the fluorescence instrument is capable of measuring the uniformity of the mixture non-invasively.

14. The system of claim 1, further comprising a second fluorescence instrument capable of measuring uniformity of the mixture during processing of the mixture.

15. The system of claim 1, further comprising a data acquisition system connected to the fluorescence instrument.

16. The system of claim 1, further comprising a data acquisition system unconnected to the fluorescence instrument and configured to receive RF signals from the RF converter.

17. A system far processing materials comprising:
a processing apparatus configured to process a mixture of more than one component;
a fluorescence instrument operatively associated with the processing apparatus capable of measuring the uniformity of the mixture during processing of the mixture; and
a switch including a position-detection mechanism designed to activate the fluorescence instrument when the processing apparatus is at a selected position.

18. The system of claim 17, wherein the switch comprises a mercury switch.

19. The system of claim 17, wherein the processing apparatus is constructed to process a mixture of pharmaceutical components.

20. The system of claim 17, wherein the processing apparatus comprises a mixing apparatus.

21. The system of claim 17, wherein the processing apparatus comprises an apparatus constructed to transport the mixture.

22. The system of claim 17, wherein the processing apparatus comprises a tablet-handling apparatus.

23. The system of claim 17, wherein the processing apparatus comprises a storage unit.

24. The system of claim 17, wherein the fluorescence instrument is mountable on the exterior of the processing apparatus.

25. The system of claim 17, wherein the fluorescence instrument includes a fiber-optic probe insertable within a processing space of the processing apparatus.

26. The system of claim 17, wherein the fluorescence instrument includes a laser.

27. The system of claim 17, wherein the fluorescence instrument is capable of measuring the uniformity of the mixture in real-time during processing of the mixture.

28. The system of claim 17, wherein the fluorescence instrument is capable of measuring the uniformity of the mixture on-line during processing of the mixture.

29. The system of claim 17, wherein the fluorescence instrument is capexble of measuring the uniformity of the mixture non-invasively.

30. The system of claim 17, further comprising a second fluorescence instrument capable of measuring uniformity of the mixture during processing of the mixture.

31. The system of claim 17, further comprising an RF converter capable of converting voltages received from the fluorescence instrument to an RF signal.

32. The system of claim 31, further comprising a data acquisition system unconnected to the fluorescence instrument and configured to receive RF signals from the RF converter.

33. The system of claim 17, further comprising a data acquisition system connected to the fluorescence instrument.

34. A system for processing materials comprising:
a processing apparatus configured to process a mixture of more than one component; and
a fluorescence instrument operatively associated with the processing apparatus capable of measuring the unilbrmity of the mixture during processing of the mixture, wherein the fluorescence instrument comprises:
a light source capable of emitting light;
a first filter positioned to permit light emitted from the light source having selected wavelengths to pass therethrough;
a dichroic mirror constructed and arranged to reflect a portion of the light passing through the first filter into a mixing apparatus designed to contain the mixture, and to permit a portion of the fluorescent light emitted from at least one component of the mixture to pass therethrough;
a second filter positioned to permit fluorescent light having selected wavelengths to pass therethrough; and
a detector capable of detecting fluorescent light passing through the second filter.

35. The system of claim 34, wherein the processing apparatus is constructed to process a mixture of pharmaceutical components.

36. The system of claim 34, wherein the processing apparatus comprises a mixing apparatus.

37. The system of claim 34, wherein the processing apparatus comprises an apparatus constructed to transport the mixture.

38. The system of claim 34, wherein the processing apparatus comprises a tablet-handling apparatus.

39. The system of claim 34, wherein the processing apparatus comprises a storage unit.

40. The system of claim 34, wherein the fluorescence instrument is mountable on the exterior of the processing apparatus.

41. The system of claim 34, wherein the fluorescence instrument includes a fiber-optic probe insertable within a processing space of the processing apparatus.

42. The system of claim 34, wherein the fluorescence instrument includes a laser.

43. The system of claim 34, wherein the fluorescence instrument is capable of measuring the uniformity of the mixture in real-time during processing of the mixture.

44. The system of claim 34, wherein the fluorescence instrument is capable of measuring the uniformity of the mixture on-line during processing of the mixture.

45. The system of claim 34, wherein the fluorescence instrument is capable of measuring the uniformity of the mixture non-invasively.

46. The system of claim 34, further comprising a second fluorescence instrument capable of measuring uniformity of the mixture during processing of the mixture.

47. The system of claim 34, further comprising an RF converter capable of converting voltages received from the fluorescence instrument to an RF signal.

48. The system of claim 47, further comprising a data acquisition system unconnected to the fluorescence instrument and configured to receive RF signals from the RF converter.

49. The system of claim 34, further comprising a data acquisition system connected to the fluorescence instrument.

50. A system for processing materials comprising:
 a processing apparatus configured to process a mixture of more than one component; and
 a fluorescence instrument operatively associated with the processing apparatus capable of non-invasively analyzing the mixture using fluorescence during processing of the mixture; and
 an RF converter capable of converting voltages received from the fluorescence instrument to an RF signal.

51. The system of claim 50, wherein the processing apparatus is constructed to process a mixture of pharmaceutical components.

52. The system of claim 50, wherein the processing apparatus comprises a mixing apparatus.

53. The system of claim 50, wherein the processing apparatus comprises an apparatus constructed to transport the mixture.

54. The system of claim 50, wherein the processing apparatus comprises a tablet-handling apparatus.

55. The system of claim 50, wherein the processing apparatus comprises a storage unit.

56. The system of claim 50, wherein the fluorescence instrument is capable of measuring the concentration of a component.

57. The system of claim 50, wherein the fluorescence instrument is capable of non-invasively analyzing the mixture in real-time during processing of the mixture.

58. The system of claim 50, wherein the fluorescence instrument is capable of non-invasively analyzing the mixture on-line during processing of the mixture.

59. A system for processing materials comprising:
 a processing apparatus configured to process a mixture of more than one component;
 a fluorescence instrument operatively associated with the processing apparatus capable of measuring the concentration of one component of the mixture during processing of the mixture; and
 a switch including a position-detection mechanism designed to activate the fluorescence instrument when the processing apparatus is at a selected position.

60. The system of claim 59, wherein the processing apparatus is constructed to process a mixture of pharmaceutical components.

61. The system of claim 59, wherein the processing apparatus comprises a mixing apparatus.

62. The system of claim 59, wherein the processing apparatus comprises an apparatus constructed to transport the mixture.

63. The system of claim 59, wherein the processing apparatus comprises a tablet-handling apparatus.

64. The system of claim 59, wherein the processing apparatus comprises a storage unit.

65. The system of claim 59, wherein the fluorescence instrument is mountable on the exterior of the processing apparatus.

66. The system of claim 59, wherein the fluorescence instrument includes a fiber-optic probe insertable within a processing space of the processing apparatus.

67. The system of claim 59, wherein the fluorescence instrument includes a laser.

68. The system of claim 59, wherein the fluorescence instrument includes a light source capable of emitting light over a range of wavelengths.

69. The system of claim 59, wherein the fluorescence instrument is capable of nicasuring the concentration of one of the components of the mixture in real-time during processing of the mixture.

70. The system of claim 59, wherein the fluorescence instrument is capable of rneasunng the concentration of one of the components of the mixture on-line during processing of the mixture.

71. The system of claim 59, wherein the fluorescence instrument is capable of measuring the concentration of one of the components of the mixture non-invasively during processing of the mixture.

72. The system of claim 59, further comprising a second fluorescence instrument capable of measuring the concentration of one of the components of the mixture during processing of the mixture.

73. The system of claim 59, wherein the switch comprises a mercury switch.

74. A system for processing materials comprising:
 a processing apparatus configured to process a mixture of more than one component; and
 a fluorescence instrument operatively associated with the processing apparatus capable of measuring the concentration of one component of the mixture during processing of the mixture; and
 an RF converter capable of converting voltages received from the fluorescence instrument to an RF signal.

75. The system of claim 59, further comprising a data acquisition system connected to the fluorescence instrument.

76. The system of claim 74, further comprising a data acquisition system unconnected to the fluorescence instrument and configured to receive RF signals from the RF converter.

77. The system of claim 74, wherein the processing apparatus is constructed to process a mixture of pharmaceutical components.

78. The system of claim 74, wherein the fluorescence instrument is mountable on the exterior of the processing apparatus.

79. The system of claim 74, wherein the fluorescence instrument includes a fiber-optic probe insertable within a processing space of the processing apparatus.

80. The system of claim 74, wherein the fluorescence instrument is capable of measuring the concentration of one component of the mixture in real-time during processing of the mixture.

81. The system of claim 74, wherein the fluorescence instrument is capable of measuring the concentration of one component of the mixture on-line during processing of the mixture.

82. The system of claim 74, wherein the fluorescence instrument is capable of measuring the concentration of one component of the mixture non-invasively.

83. The system of claim 74, further comprising an RF converter capable of converting voltages received from the fluorescence instrument to an RF signal.

84. The system of claim 83, further comprising a data acquisition system unconnected to the fluorescence instrument and configured to receive RF signals from the RF converter.

85. The system of claim 74, further comprising a data acquisition system connected to the fluorescence instrument.

86. A system for processing materials comprising:
a processing apparatus configured to process a mixture of more than one component; and
a fluorescence instrument operatively associated with the processing apparatus capable of measuring the concentration of one component of the mixture during processing of the mixture, wherein the fluorescence instrument comprises:
 a light source capable of emitting light;
 a first lifter positioned to permit light emitted from the light source having selected wavelengths to pass therethrough;
 a dichroic mirror constructed and arranged to reflect a portion of the light passing through the first filter into a mixing apparatus designed to contain the mixture, and to permit a portion of the fluorescent light emitted from at least one component of the mixture to pass therethrough;
 a second filter positioned to permit fluorescent light having selected wavelengths to pass therethrough; and
 a detector capable of detecting fluorescent light passing through the second filter.

87. The system of claim 86, wherein the processing apparatus is constructed to process a mixture of pharmaceutical components.

88. The system of claim 86, wherein the fluorescence instrument is mountable on the exterior of the processing apparatus.

89. The system of claim 86, wherein the fluorescence instrument includes a fiber-optic probe insertable within a processing space of the processing apparatus.

90. The system of claim 86, wherein the fluorescence instrument is capable of measuring the concentration of one component of the mixture in real-time during processing of the mixture.

91. The system of claim 86, wherein the fluorescence instrument is capable of measuring the concentration of one component of the mixture on-line during processing of the mixture.

92. The system of claim 86, wherein the fluorescence instrument is capable of measuring the concentration of one component of the mixture non-invasively.

93. The system of claim 86, further comprising an RF converter capable of converting voltages received from the fluorescence instrument to an RF signal.

94. The system of claim 93, further comprising a data acquisition system unconnected to the fluorescence instrument and configured to receive RF signals from the RF converter.

95. The system of claim 86, frirther comprising a data acquisition system connected to the fluorescence instrument.

* * * * *

UNITED STATES PATENT AND TRADEMARK OFFICE
CERTIFICATE OF CORRECTION

PATENT NO. : 6,791,688 B2
DATED : September 14, 2004
INVENTOR(S) : Lai et al.

It is certified that error appears in the above-identified patent and that said Letters Patent is hereby corrected as shown below:

Column 17,
Line 33, please replace "far" with -- for --.

Column 20,
Line 10, please replace "nicasuring" with -- measuring --.
Line 14, please replace "rneasunng" with -- measuring --.

Signed and Sealed this

Twenty-first Day of December, 2004

JON W. DUDAS
*Director of the United States Patent and Trademark Office*